United States Patent [19]

Gertner et al.

[11] Patent Number: 5,324,521
[45] Date of Patent: Jun. 28, 1994

[54] SYSTEMS FOR TRANSDERMAL ADMINISTRATION OF MEDICAMENTS

[75] Inventors: Avi Gertner, Kfar Saba; Yosef Rubinstein, Nes Ziona, both of Israel

[73] Assignee: Dermamed, Nes Ziona, Israel

[21] Appl. No.: 929,485

[22] Filed: Aug. 18, 1992

Related U.S. Application Data

[63] Continuation of Ser. No. 653,393, Feb. 11, 1991, abandoned, which is a continuation-in-part of Ser. No. 451,679, Dec. 18, 1989, Pat. No. 5,049,143.

[51] Int. Cl.$^5$ .............................................. A61K 9/70
[52] U.S. Cl. .................... 424/449; 424/434; 424/443; 424/444; 424/447; 424/484; 604/304
[58] Field of Search .............. 424/449, 447, 443, 444, 424/484; 604/304

[56] References Cited

U.S. PATENT DOCUMENTS

| | | | |
|---|---|---|---|
| 3,942,480 | 3/1976 | Hair et al. | 119/156 |
| 3,970,080 | 7/1976 | White | 119/156 |
| 3,996,934 | 12/1976 | Zaffaroni | 424/434 |
| 4,026,290 | 5/1977 | Brooker | 604/290 |
| 4,221,189 | 9/1980 | Olvera | 119/96 |
| 4,428,327 | 1/1984 | Steckel | 119/156 |
| 4,435,180 | 3/1984 | Leeper | 424/449 X |
| 4,486,194 | 12/1984 | Ferrara | 424/449 |
| 4,506,630 | 3/1986 | Hair | 119/156 |
| 4,585,797 | 4/1986 | Cioca | 604/304 |
| 4,620,849 | 11/1986 | Corner | 604/290 |
| 4,638,043 | 10/1987 | Szycher et al. | 528/75 |
| 4,725,279 | 2/1988 | Woodroof | 128/156 X |
| 4,767,402 | 8/1988 | Kost et al. | 604/22 |
| 4,775,372 | 10/1988 | Wilberg | 604/290 |
| 4,777,047 | 10/1988 | Bauer et al. | 424/449 |
| 4,792,450 | 12/1988 | Kydonieus | 424/449 |
| 4,818,540 | 4/1989 | Chien | 424/449 |
| 4,820,525 | 4/1989 | Leonard et al. | 424/486 |
| 4,822,617 | 4/1989 | Panoz | 604/304 |
| 4,879,297 | 11/1989 | Mahjour et al. | 514/282 |
| 4,908,389 | 3/1990 | Mahjour et al. | 514/772 |
| 4,930,451 | 6/1990 | Miller et al. | 119/156 |
| 5,059,427 | 10/1991 | Yoshida et al. | 424/449 |

FOREIGN PATENT DOCUMENTS

| | | |
|---|---|---|
| 28462/77 | 3/1979 | Australia . |
| 66647/81 | 8/1981 | Australia . |
| 79545/82 | 8/1982 | Australia . |
| 79212/82 | 1/1983 | Australia . |
| 31850/84 | 2/1985 | Australia . |
| 39352/85 | 5/1986 | Australia . |
| 60222/86 | 9/1987 | Australia . |
| 166990 | 4/1972 | New Zealand . |
| 178922 | 12/1977 | New Zealand . |
| 179341 | 12/1977 | New Zealand . |
| 200232 | 8/1985 | New Zealand . |
| 206173 | 4/1986 | New Zealand . |
| 204870 | 6/1986 | New Zealand . |
| 207874 | 1/1987 | New Zealand . |

(List continued on next page.)

OTHER PUBLICATIONS

Pitman, I. H., et al, "Topical Drug Delivery to Cattle and Sheep", Jour. of Pharm. Sci., vol. 70, No. 11, Nov., 1981, pp. 1181–1193.

Pitman, I. H., et al, "A Comparison of Frozen and Reconstituted Cattle and Human Skin as Barriers . . . ", Jour. of Pharm. Sci., vol. 71, No. 4, Apr., 1982, pp. 427–430.

Primary Examiner—Thurman K. Page
Assistant Examiner—Roy Bawa
Attorney, Agent, or Firm—Browdy and Neimark

[57] ABSTRACT

A non-adhesive matrix for use as a dosage form in the transdermal administration of a medicament to a mammal comprises a porous, non-adhesive, absorbent perforate solid support having absorbed thereon a mixture comprising a medicament adapted for transdermal administration and a pharmaceutically acceptable carrier for the medicament. The carrier consists essentially of at least one compound selected from esters of $C_{8-24}$ fatty acids, pharmaceutically acceptable aliphatic polyhydroxy compounds and non-volatile paraffins.

4 Claims, 19 Drawing Sheets

FOREIGN PATENT DOCUMENTS

| | | |
|---|---|---|
| 208597 | 2/1987 | New Zealand . |
| 209843 | 3/1987 | New Zealand . |
| 210356 | 4/1987 | New Zealand . |
| 208692 | 3/1988 | New Zealand . |
| 210689 | 8/1988 | New Zealand . |
| 210690 | 8/1988 | New Zealand . |
| 214496 | 3/1989 | New Zealand . |
| 215746 | 8/1989 | New Zealand . |
| 222761 | 10/1989 | New Zealand . |
| 221991 | 12/1989 | New Zealand . |
| 225907 | 5/1990 | New Zealand . |
| 224682 | 6/1990 | New Zealand . |
| 224707 | 9/1990 | New Zealand . |
| 228637 | 10/1990 | New Zealand . |
| 228562 | 5/1991 | New Zealand . |
| 226209 | 6/1991 | New Zealand . |
| 231907 | 10/1991 | New Zealand . |
| 231908 | 10/1991 | New Zealand . |
| 228533 | 1/1992 | New Zealand . |
| 1515925 | 6/1978 | United Kingdom . |
| 1519149 | 7/1978 | United Kingdom . |
| 87/04936 | 8/1987 | World Int. Prop. O. . |

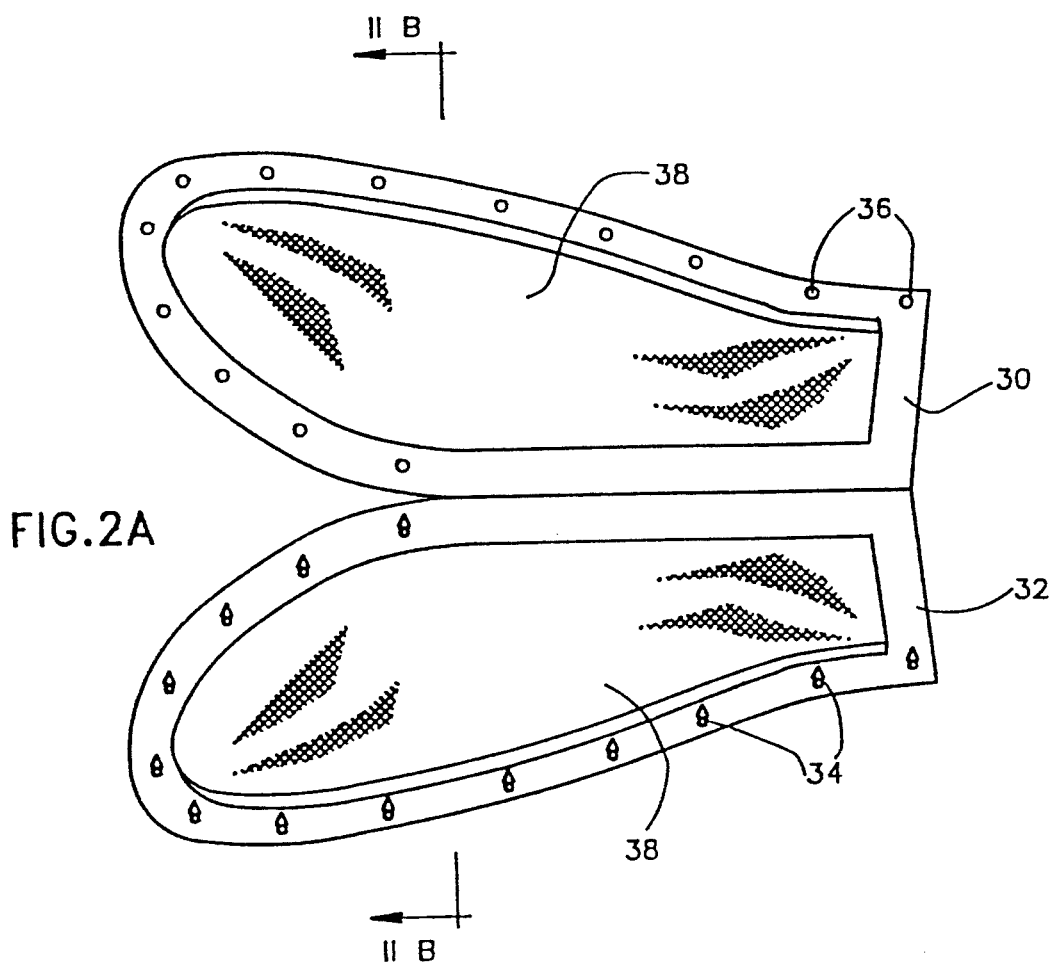
FIG. 2A
FIG. 2B
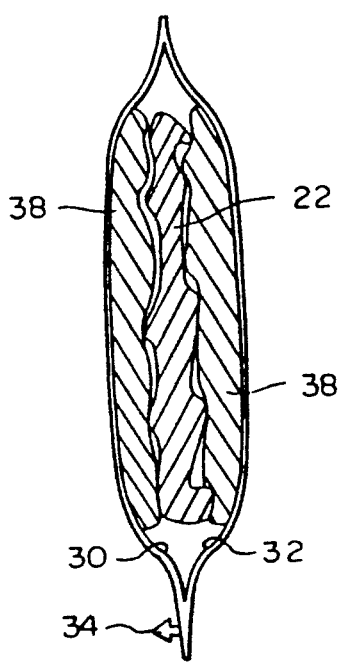

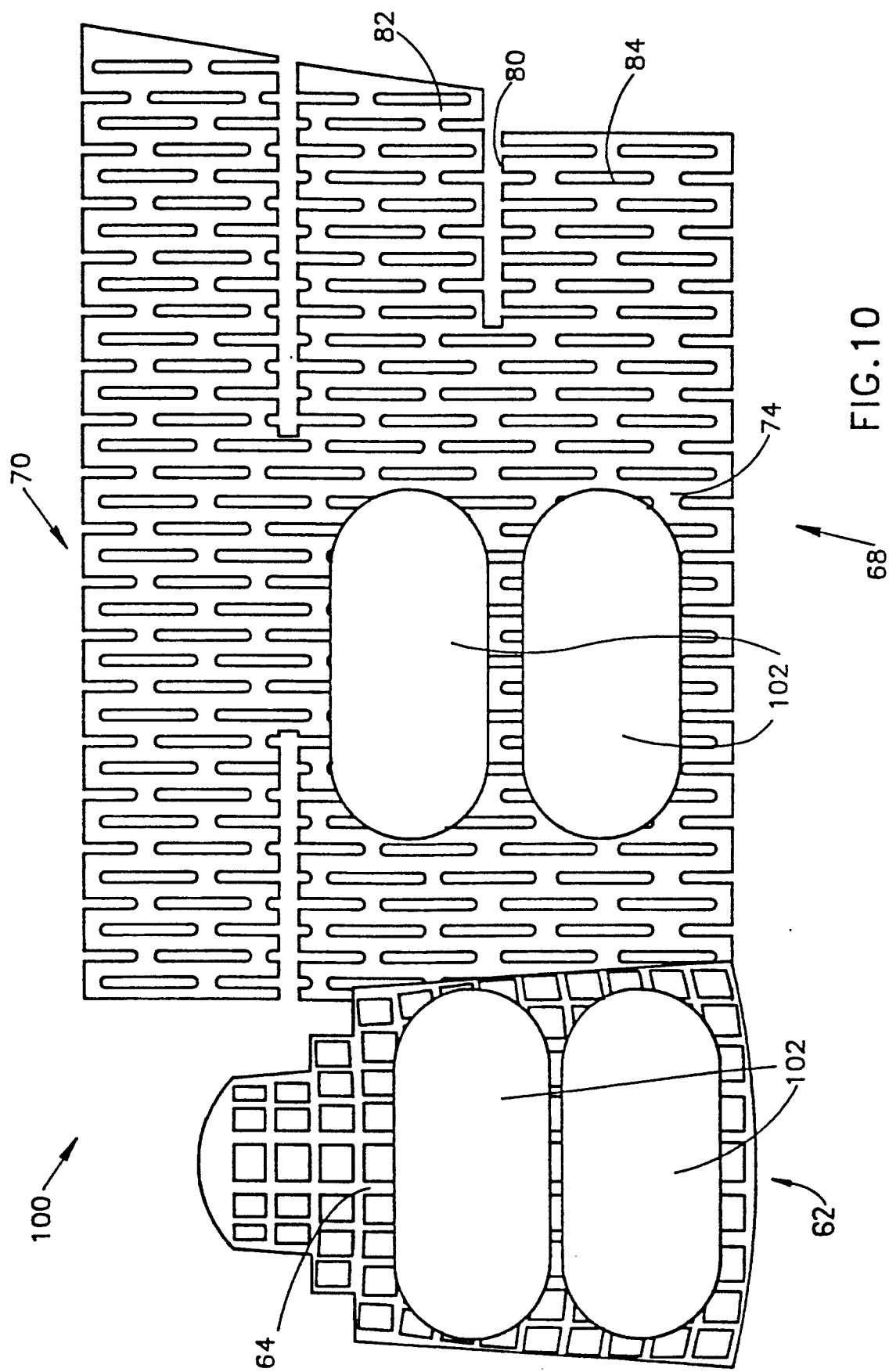

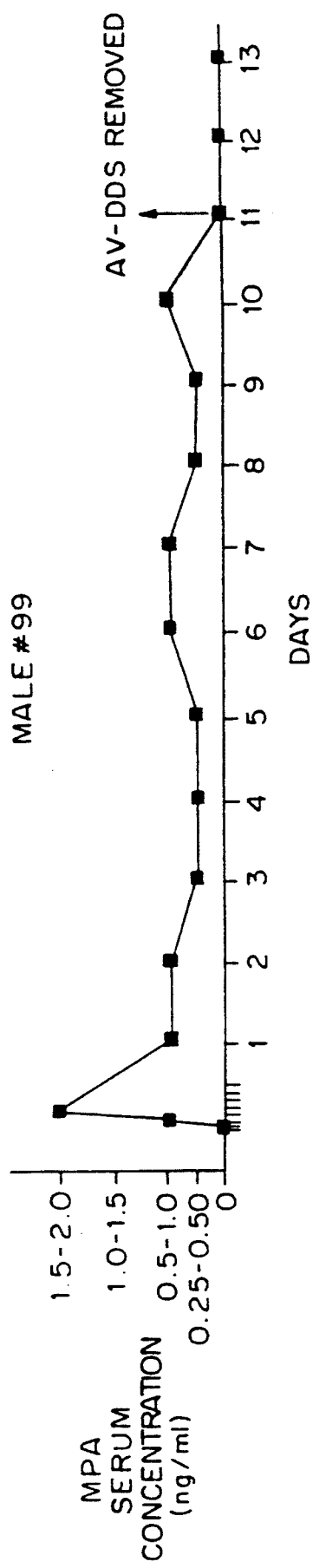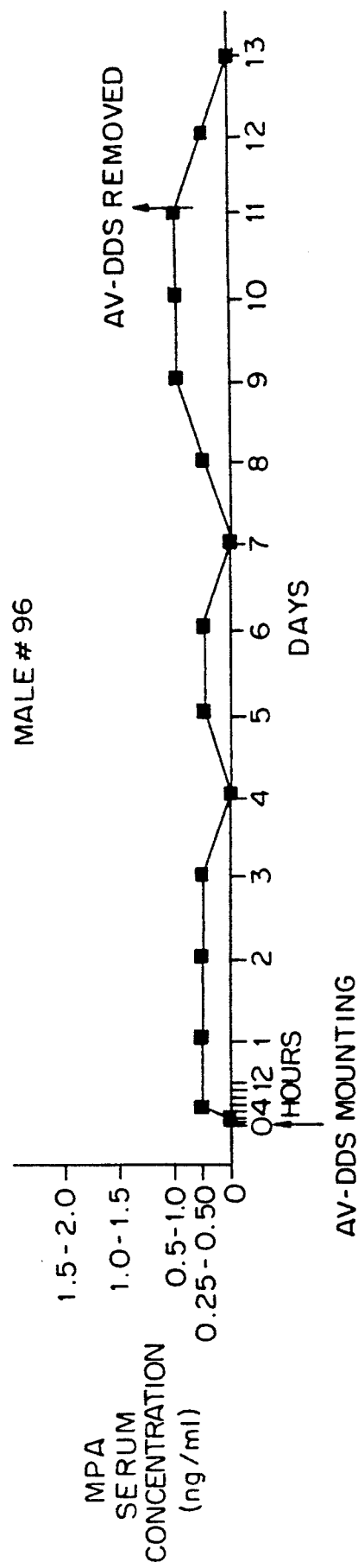

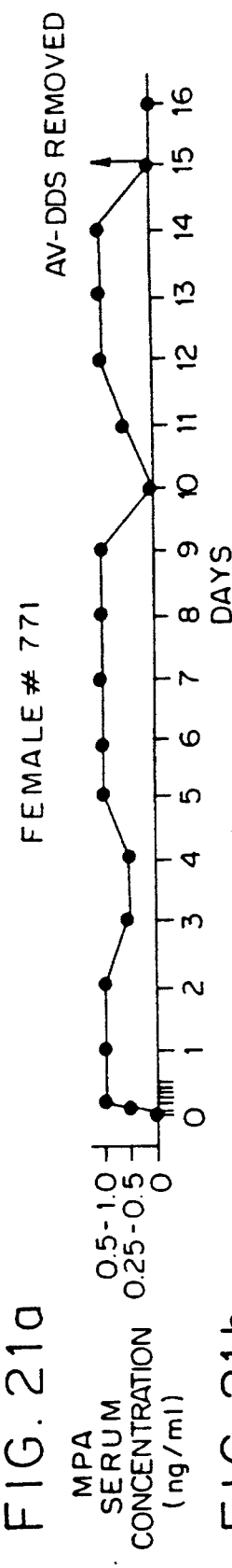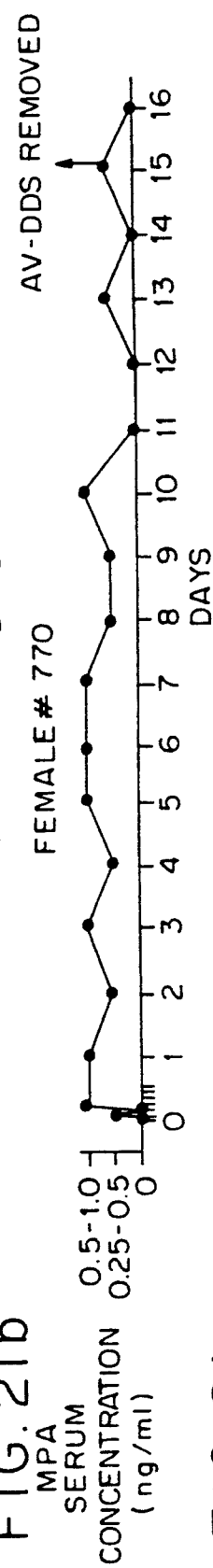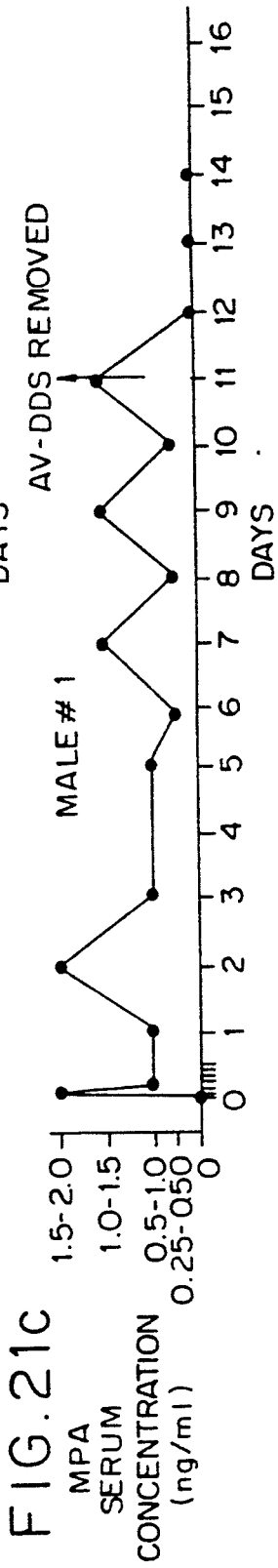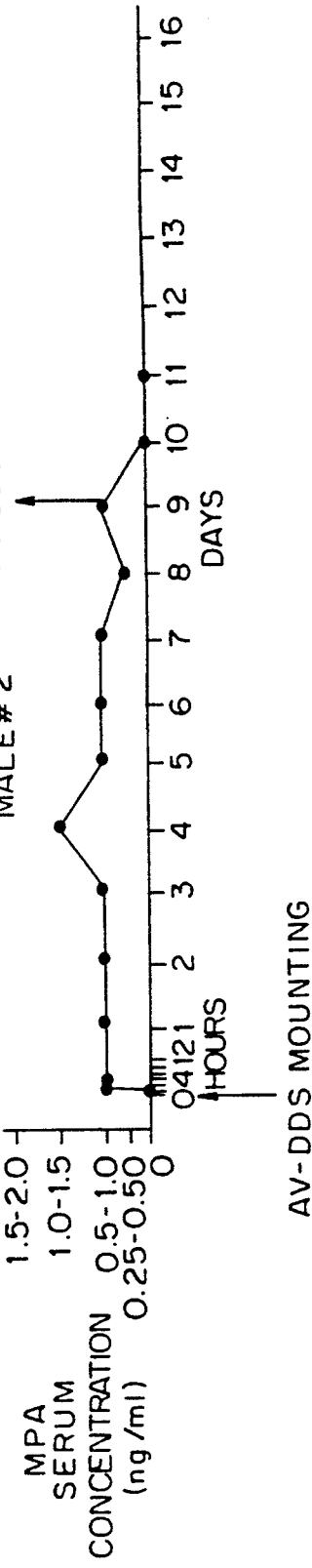

SYSTEMS FOR TRANSDERMAL ADMINISTRATION OF MEDICAMENTS

This application is a continuation of application Ser. No. 07/653,393, filed Feb. 11, 1991 and now abandoned, which is a continuation-in-part of Ser. No. 07/451,679 filed Dec. 18, 1989 and in U.S. Pat. No. 5,049,143.

FIELD AND BACKGROUND OF THE INVENTION

The present invention relates to a matrix incorporating medicaments for transdermal administration, particularly but not exclusively in the field of animal husbandry and to apparatus and techniques for administering veterinary medicaments transdermally.

Various techniques and devices are known for administering medicaments through the skin, particularly for veterinary use. One example of such a technique is described in U.S. Pat. No. 4,026,290, which suggests attachment of a device to the ears or tail of the animal for applying motion sickness mitigators, anti-migraine compounds, analgesics, anthelmintics, antiprotozoal compounds and systemic insecticides, miticide and acaricides.

Transdermal drug delivery in veterinary applications is discussed in an article entitled "Topical Drug Delivery to Cattle and Sheep" by Ian H. Pitman and Susan J. Rostas, in Journal of Pharmaceutical Sciences, Vol. 70, No. 11, November, 1981, pp. 1181–1193 and in an article by the same authors entitled "A Comparison of Frozen and Reconstituted Cattle and Human Skin as Barriers to Drug Penetration", in Journal of Pharmaceutical Sciences, Vol. 71, No. 4, April, 1982, pp 427–430. Transdermal drug delivery has been proposed for administering prophylactic medicaments in veterinary contexts but, to the best of the knowledge of the inventors, has not had any practical application of significance in veterinary practice.

Growth radiators and growth promoters, here collectively termed "growth promoters", are commonly used in veterinary applications and are often applied using implants which cannot be conveniently removed prior to slaughter. Hormones for synchronization in mammals are generally administered vaginally, a technique which requires skill and involves potential damage to the animal and could result in infertility.

In U.S. Pat. No. 4,638,043 (Szycher et al), there is disclosed a polyurethane matrix for dispensing drugs dispersed therein, primarily for incorporation in a medical patch comprised of successive layers of a substrate, a pressure sensitive adhesive, the drug dispensing matrix and optionally a second layer of adhesive. The matrix may also include (e.g.) polypropylene glycol, polyethylene glycol or glycerine, to soften layer softer and to aid the transport of the drug out of the matrix and into the skin.

As acknowledged in U.S. Pat. No. 4,767,402 (Kost et al), which discloses the use of ultrasound for enhancing transdermal drug delivery, relatively few drugs are known to be deliverable transdermally, insofar as the majority of drugs will not penetrate the skin at rates sufficiently high for therapeutic efficacy.

U.S. Pat. No. 4,792,450 (Kydonieus et al) discloses a transdermal drug delivery device which comprises a vinyl gel layer comprising PVC and a drug uniformly dispersed therein, the vinyl gel layer comprising a primary plasticizer for the PVC and an organic nonvolatile gel forming additive in an amount sufficient to form a gel. Examples of such additives are isopropyl palmirate, isopropyl myristate, soybean oil, castor oil, linseed oil, olive oil, mineral oil, petrolatum, caprylic/capric triglyceride and non-ionic surfactants.

In U.S. Pat. No. 4,818,540 (Chien et al), there is disclosed essentially a transdermal fertility-controlling polymer matrix dosage unit comprising an impervious backing layer, a polymer matrix disc layer adhered thereto containing microdispersed fertility-controlling estrogen and progestin hormones, and an adhesive layer for securing the dosage unit to the subject. The device may contain, preferably in the adhesive layer, but alternatively or additionally in the matrix layer, a skin permeation enhancing agent, in particular a fatty acid $CH_3(CH_2)_nCOOH$, where n is 2–16, isopropyl myristate or decyl methyl sulfoxide.

U.S. Pat. No. 4,820,525 (Leonard et al) discloses the use of a foamed polyethylene having specified properties, as a drug reservoir in a transdermal/transmucosal pharmaceutical delivery system. Thus, fertility hormones and albuterol were applied transdermally from such reservoirs attached to adhesive tape across nude mouse skin or cadaver skin, using menthol as penetration enhancer.

In U.S. Pat. No. 4,822,617 (Panoz), there is disclosed a device for the transdermal administration of skin-permable drugs (e.g. nitroglycerin, clonidin, methadone and scopolamine) in an ointment, cream or jelly-like carrier, comprising a laminar applicator adapted to receive a predetermined quantity of the drug on a skin-contacting surface thereof, the latter being overlaid by a drug-impervious layer to ensure a unidirectional transfer of the drug to the skin surface. In an exemplified embodiment, the applicator is loaded with a predetermined amount of ointment containing 2% nitroglycerin and lactose in an absorptive lanolin and white petrolatum base formulated to provide controlled release of the active ingredient. The entire contents of all of the foregoing U.S. patents are incorporated by reference herein.

It will be appreciated that adhesive patches, by means of which drugs are conventionally administered transdermally to humans, can result in skin irritation and sensitization with prolonged use. Shaving the hair from a suitable area may also be necessary. Adhesive patches would be quite unsuitable for animals, partly because of the great quantity of body hair in comparison with humans, and partly because adhesive patches would be liable to be rubbed off. By contrast, the present matrices can conveniently be used for transdermal administration to animals, by means of the devices described herein. Moreover, persons skilled in the art can readily appreciate that these matrices could also be readily adapted for human use, e.g. by securing to the arm or leg by a bandage which is impervious to the drug/carrier combination.

It may further be noted that the sense of the most of the prior art in relation to transdermal administration to humans is that only a restricted number of drugs are inherently suitable for this form of administration. It is believed that the present invention offers a means of transdermal delivery of a wider spectrum of drugs than has heretofore been made generally available, particularly to animals, but also to humans.

As indicated above, adhesive plasters incorporating medicaments for transdermal administration, which are known for application to humans, would be generally inappropriate for veterinary use.

SUMMARY OF THE INVENTION

The present invention seeks to provide a matrix incorporating medicaments for transdermal administration, particularly but not exclusively in the field of animal husbandry, as well as techniques and apparatus for veterinary transdermal application of medicaments. The present invention accordingly provides a matrix for transdermal administration of a medicament in a non-adhesive context, which comprises a porous, absorbent perforate solid support, having absorbed thereon a medicament adapted for transdermal administration and a transdermally transporting effective amount of a carrier for the medicament comprising at least one compound selected from esters of $C_{8-24}$ fatty acids, pharmaceutically acceptable aliphatic polyhydroxy compounds and non-volatile paraffins. The at least one fatty acid may be saturated or ethylenically unsaturated.

The perforations in the support matrix enable the user to impart a predetermined desired degree of "breathability" thereto, since even a porous but imperforate matrix may not be adequately breathable so long as the matrix pores at the skin surface are filled with a medicament/carrier combination. The matrix of the invention possesses the general advantages that it enables one medicament, or multiple medicaments simultaneously, to be administered transdermally, for a sustained period, with rapid penetration of the skin and without any shaving or other pretreatment. Unlike much of the prior art, it seems that the invention is generally operable without using skin penetration enhancers. Further advantages of the invention in contrast with some of the prior art methods, are that is unnecessary to adjust the pH of the administered composition, or to ensure that the administered medicament is completely soluble in the carrier; preparation of the compositions is uncomplicated; and the same or similar carriers are effective for different kinds of drugs.

The combination of medicament and carrier will preferably be in the liquid state at ambient temperatures, although the invention also extends to such combinations which are semi-solid or semi-liquid. Persons skilled in the art will be aware that combinations of medicament and carrier in the liquid state, for transdermal administration, whether to animals or humans, are relatively rare in practical terms.

The present invention further provides in accordance with a preferred embodiment thereof, a technique for administering medicaments transdermally in veterinary applications comprising the steps of non-adhesively applying a medicament to the skin of an animal and non-surgically terminating the application of the medicament at a pre-determined time, wherein the medicament is in the form of a matrix defined herein. Termination of the application of the medicament may be precisely timed so as to prevent residues of the medicament from remaining in the tissues of the animal or in food products produced thereby, such as milk. Additionally in accordance with a preferred embodiment of the present invention, the step of non-surgically terminating the application of the medicament takes place at least a pre-determined length of time before slaughter of the animal for preventing more than a pre-determined threshold of the residue of the medicament from remaining in the slaughtered animal.

BRIEF DESCRIPTION OF THE DRAWINGS

The present invention will be understood and appreciated more fully from the following detailed description taken together with the drawings in which:

FIGS. 2A and 2B are respective pictorial and sectional illustrations of a removable enclosure for transdermal application of medicaments to the ear of an animal in accordance with another preferred embodiment of the present invention, FIG. 2A illustrating the enclosure in an opened orientation, and FIG. 2B, illustrating the enclosure in a closed orientation.

FIGS. 9 and 10 are pictorial illustrations of the front and back respectively of experimental apparatus for applying a medicament transdermally to an animal ear employed in the Examples set forth hereinbelow;

FIGS. 11A, 11B, 11C, 11D and 11E are illustrations taken along lines A—A, B—B, C—C, D—D and in the direction E in FIG. 5;

FIGS. 20 and 21 depict the variation of medroxyprogesterone acetate serum levels with time, following administration in accordance with embodiments of the invention.

DETAILED DESCRIPTION OF THE INVENTION

Figure 1A:
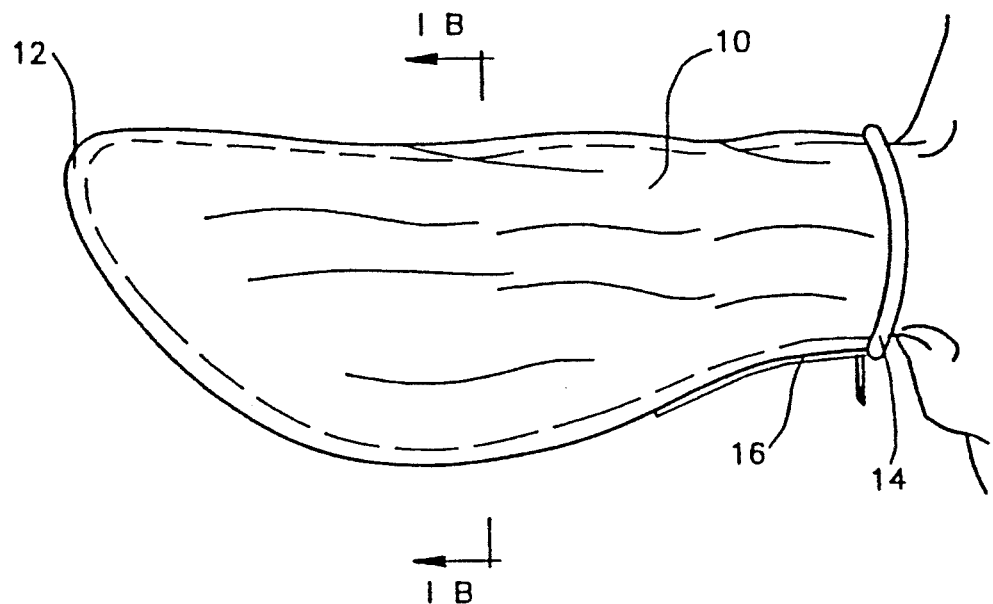
FIGS. 1A and 1B are respective pictorial and sectional illustrations of a removable enclosure for transdermal application of medicaments to the ear of an animal in accordance with a preferred embodiment of the present invention.

The medicaments utilized herein may be any medicament adapted for transdermal administration and may include, for example, growth promoters, fertility agents including medicaments for the control of ovulation in breeding animals, micronutritional supplements such as vitamins and trace elements, anthelmintics, antibiotics, antiparasitics and antiinflammatory agents.

In accordance with a particular embodiment of the invention the medicament is an agent for the control of ovulation in breeding animals and the steps of applying and non-surgically terminating application of the medicament occur at preselected times which are Synchronized for a herd.

Additionally in accordance with a preferred embodiment of the invention there is provided apparatus for transdermal administration by application of medicaments non-adhesively to the skin of animals comprising a removable enclosure arranged to be non-invasively mounted onto an animal ear, and incorporating a matrix in accordance with the invention.

In accordance with one embodiment of the invention, the aforementioned enclosure comprises an enclosure arranged to fit over the ear and having a selectable closure associated therewith. The selectable closure may comprise, for example, a zip fastener, or an arrangement of clips or other fasteners which engage each other peripherally of the ear. According to an alternative embodiment of the invention, the removable enclosure may comprise a pair of members which are urged together in engagement by a resilient device.

In accordance with a preferred embodiment of the invention, the removable enclosure is arranged to apply medicaments to two opposite surfaces of the ear. Alternatively, a medicament may be applied on only one of the opposite surfaces. As further alternatives, more than one medicament may be applied on a given surface or two or more different medicaments may be applied on different surfaces of the enclosure. As yet a further alternative, different medicaments may be applied to different ears of the animal. It is a particular feature of the present invention that no aseptic or other preparation of the animal is required prior to application of the medicament, inasmuch as the enclosure may be mounted on an unprepared and untreated ear.

In accordance with a preferred embodiment of the invention, the removable enclosure is arranged such that in normal application and use, the medicament does not come into physical contact with a person applying or removing the enclosure. In accordance with another preferred embodiment of the invention, the matrix may be configured to provide a desired controlled or sustained release pattern. It is a particular preferred feature of the invention that the removable enclosure provides a visual indication of which animals are being treated. Suitable color or pattern coding may be provided on the enclosure to indicate the type and/or duration of treatment.

The pharmaceutical compositions described herein for the transdermal administration of medicaments are believed to be per se novel and inventive. Such compositions, which comprise an effective amount of a medicament adapted for transdermal administration, in combination with a transdermally transporting effective amount of a carrier for the medicament which is liquid at ambient temperatures and which comprises at least one compound selected from esters of $C_{8-24}$ fatty acids, pharmaceutically acceptable aliphatic polyhydroxy compounds and non-volatile paraffins, thus constitute a further aspect of the invention.

In accordance with a preferred embodiment of the invention, the medicament is a growth promoter. In accordance with another preferred embodiment of the invention, the medicament is a fertility drug. In accordance with yet another preferred embodiment of the invention, the medicament is a fertility synchronization agent. Additionally in accordance with another preferred embodiment of the invention, the medicament is a micronutritional supplement. Alternatively in accordance with another preferred embodiment of the invention, the medicament is an anti-inflammatory agent. In accordance with yet other preferred embodiments of the invention, the medicament is selected from anthelmintics, antibiotics and antiparasitics.

Non-limiting examples of medicaments which may be utilized in accordance with the invention are: (a) fertility and growth promoting agents: estradiol, flugestone acetate, medroxyprogesterone, medroxyprogesterone acetate, megestrol acetate, progesterone, proligestone, melengestrol acetate, testosterone, trenbulone, zeranol; (b) anthelmintics: albendazole, febantel, fenbendazole, flubendazole, ivermectin, levamisole, mebendazole, oxybendazole, oxfendazole, thiabendazole, tricalbendazole, pyrantel, morantel; (c) antibiotics: semisynthetic penicillins such as ampicillin, tetracyclines such as oxytetracycline, and cephalosporins such as cephalexin; (d) antiparasitics: cythioate, fenthion; (e) antiinflammatory agents: betamethazone, flumethazone, dexamethazone; (f) micronutrients: selenium disulfide, iron dextran.

As mentioned above, a carrier for the medicament to be administered transdermally comprises at least one ester of at least one saturated or ethylenically unsaturated $C_{8-24}$ fatty acid. The alcohol component of the ester may be derived from an aliphatic alcohol (monohydric or polyhydric) containing preferably 1-12 carbon atoms, more preferably 1-6 carbon atoms, and 1-3 hydroxy groups, in the molecule. Thus, e.g., the esters may be methyl, ethyl, propyl, isopropyl, butyl, hexyl, octyl, decyl or dodecyl esters, or esters with polyhydric alcohols such as ethylene glycol, polypropyleneglycol, glycerol or pentaerythritol.

Non-limiting examples of the acid component of the ester are caprylic, captic, lauric, palmic, stearic, arachidic, behenic, lignoceric, oleic, elaidic, petroselinic, linoleic, alpha-linolenic (9,12,15-octadecatrienoic acid), gamma-linolenic, linolelaidic, arachidic, 11-eicosenoic, 11,14-eicosadienoic, 11,14,17-eicosatrienoic, 8,11,14,-eicosatrienoic, arachidonic, 5,8,11,14,17-eicosapentaenoic, erucic and nervonic acids. According to a particular embodiment of the present invention, the carrier for the medicament comprises monoglycerides, diglycerides, triglycerides, or mixtures thereof, of at least one $C_{8-24}$ fatty acid.

Without detracting from the generality of the carrier component of the matrix of the invention, it will be convenient to use the commercially available natural fats and oils, whether of animal or vegetable origin, which contain mixtures of triglycerides of the $C_{18-24}$ fatty acids and of $C_{8-17}$ fatty acids including caprylic, captic, lauric, myristic, palmitic and heptadecanoic acids.

While the carrier components of the matrices of the invention are selected for their ability to transport medicaments transdermally, some of them may possess undesirable side effects, particularly an irritant effect on the skin which may cause swelling and discomfort. In such cases, skilled persons will be aware of the possibility of mitigating such side-effects by the addition of e.g. anti-inflammatory agents.

Soybean oil has been found by the inventors to be particularly useful as a medicament carrier in the present context, and their experience has been that this oil is compatible with the skin and does not e.g. cause inflammation or swelling. In certain cases, the addition to the carrier of agents such as an antihistamine to prevent local irritation, or an antiinflammatory agent to inhibit inflammation, may be desirable to enhance skin-compatibility, and to enable the carrier to be utilizable from a practical point of view, in accordance with the invention.

Accordingly, having regard to the constitution of soybean oil, there may be utilized as a carrier according to one embodiment of the invention a natural oil in which a major proportion of the fatty acid content consists of $C_{18-24}$ polyunsaturated fatty acids, i.e. such acids having two or more ethylenic bonds in the molecule. More preferably, a major proportion of said fatty acid content is selected from linoleic and linolenic acids.

There is also provided in accordance with a preferred embodiment of the present invention a technique for administering medicaments transdermally in veterinary applications comprising the steps of applying a medicament non-adhesively (in the form of a matrix as defined herein) to the skin of an animal and non-surgically terminating the application of the medicament at a pre-determined time.

The termination of the application of the medicament may be precisely timed so as to prevent residues of the medicament from remaining in the tissues of the animal or in food products produced thereby, such as milk.

Additionally in accordance with a preferred embodiment of the present invention, the step of non-surgically terminating the application of the medicament takes place at least a pre-determined length of time before slaughter of the animal for preventing more than a pre-determined threshold of the residue of the medicament from remaining in the slaughtered animal.

In accordance with a preferred embodiment of the invention the medicament is an agent for the control of ovulation in breeding animals and the steps of applying and non-surgically terminating application of the medicament occur at preselected times which are synchronized for a herd.

In accordance with a preferred embodiment of the invention, the removable enclosure and the medicament pad are arranged such that in normal application and use, the medicament does not come into physical contact with a person applying or removing the enclosure.

DESCRIPTION OF ILLUSTRATED EMBODIMENTS

Figure 1B:
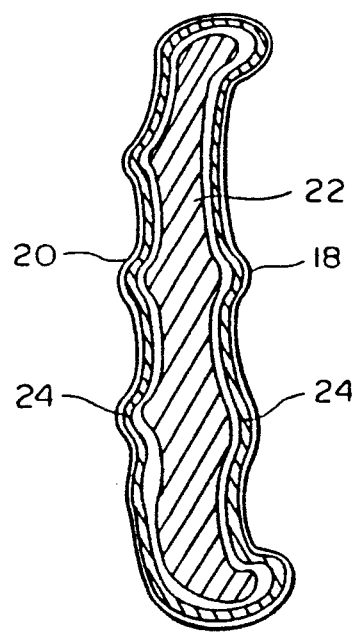

Reference is now made to FIGS. 1A and 1B which illustrate one embodiment wherein a removable enclosure 10 is provided for fitting over the ear of the animal. The enclosure 10 may typically be formed in the general configuration of a sleeve having a closed outer end 12 and an open inner end 14. Adjacent the inner end 14 there is provided a fastener 16, such as a zipper or any other type of suitable fastener such as snaps, for retaining the enclosure 10 on the ear of an animal.

According to a preferred embodiment of the invention, the enclosure 10 (which may be made from a plastic or partially plastic material such as a thermoplastic material, for example, PVC, nylon, polypropylene, polyethylene or polyester) defines two generally planar surfaces 18 and 20 which contact the respective facing planar surfaces of the ear 22 of the animal. In a particular embodiment, as illustrated, there is provided a layer 24 of the medicament-bearing porous, absorbent perforate solid support, fabricated from e.g., a synthetic polymeric or semisynthetic (such as cellulose-derived) material, or any other suitable type of porous, absorbent perforate solid support. It is preferred that layer 24 be configured to allow good exposure of the animal skin to the air, in order to prevent an adverse effect on the skin such as inflammation, when the medicament/carrier combination is in contact with the skin.

Reference is now made to FIGS. 2A and 2B which illustrate an alternative embodiment of enclosure 10. Here, the enclosure comprises two joined leaves 30 and 32 having associated fasteners 34 which engage apertures 36. A medicament-bearing porous, absorbent perforate solid support, 38, is typically associated with each of leaves 30 and 32.

Figure 3A:
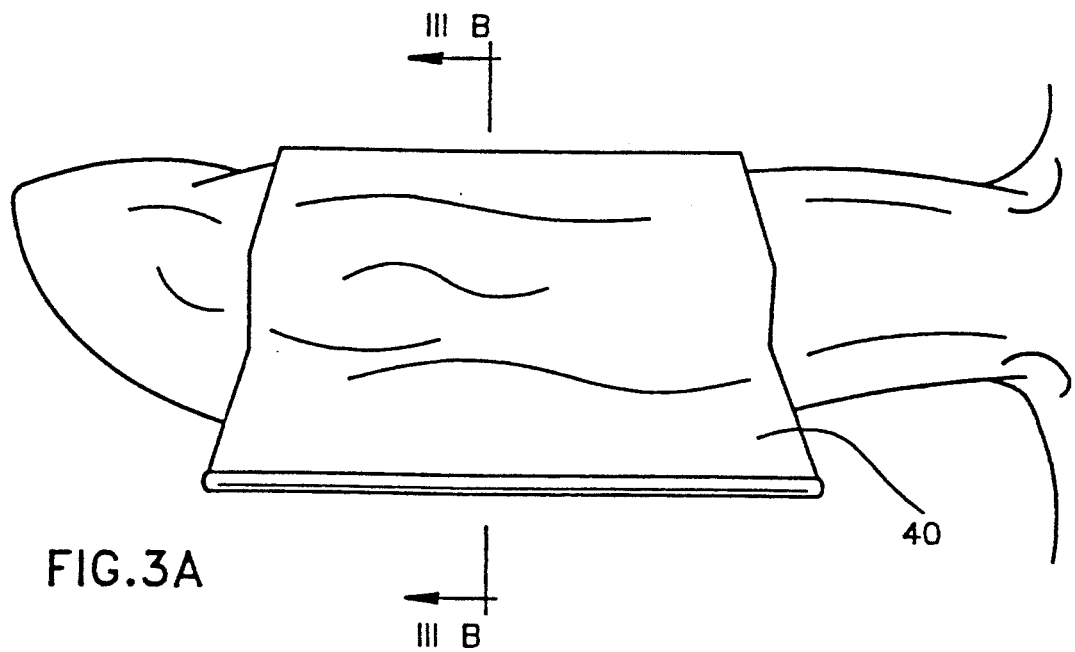
FIGS. 3A and 3B are respective pictorial and sectional illustrations of a removable enclosure for transdermal application of medicaments to the ear of an animal in accordance with yet another preferred embodiment of the present invention.
Figure 3B:
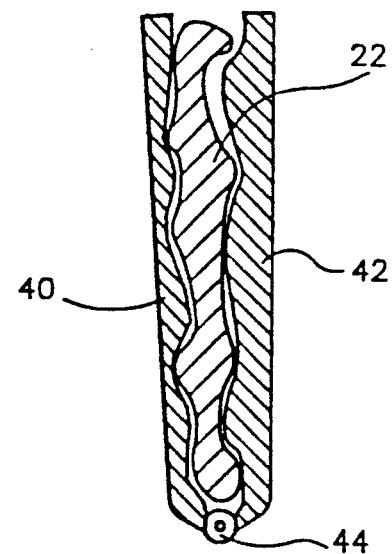

Reference is now made to FIGS. 3A and 3B, which illustrate yet another alternative embodiment of the invention wherein the enclosure is not a closed enclosure but rather comprises two leaves 40 and 42 which are arranged in a folded orientation surrounding a portion of an animal ear 22. The two leaves 40 and 42 are typically urged towards each other, thus grasping the ear 22, by means of a conventional coil spring mechanism 44. This embodiment of course includes a medicament-bearing porous, absorbent perforate solid support.

Figure 4:
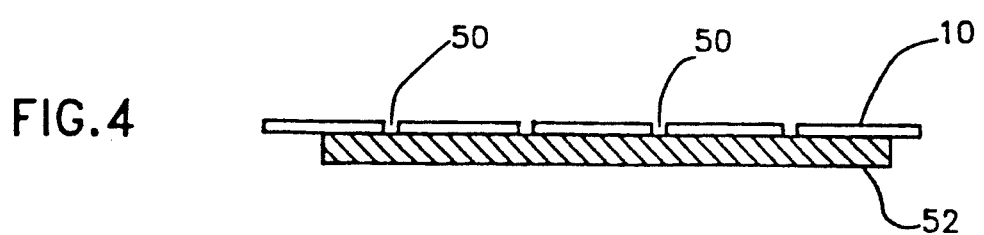
FIG. 4 is an enlarged sectional illustration of part of the enclosure of any of FIGS. 1A-3B.
Figure 5:
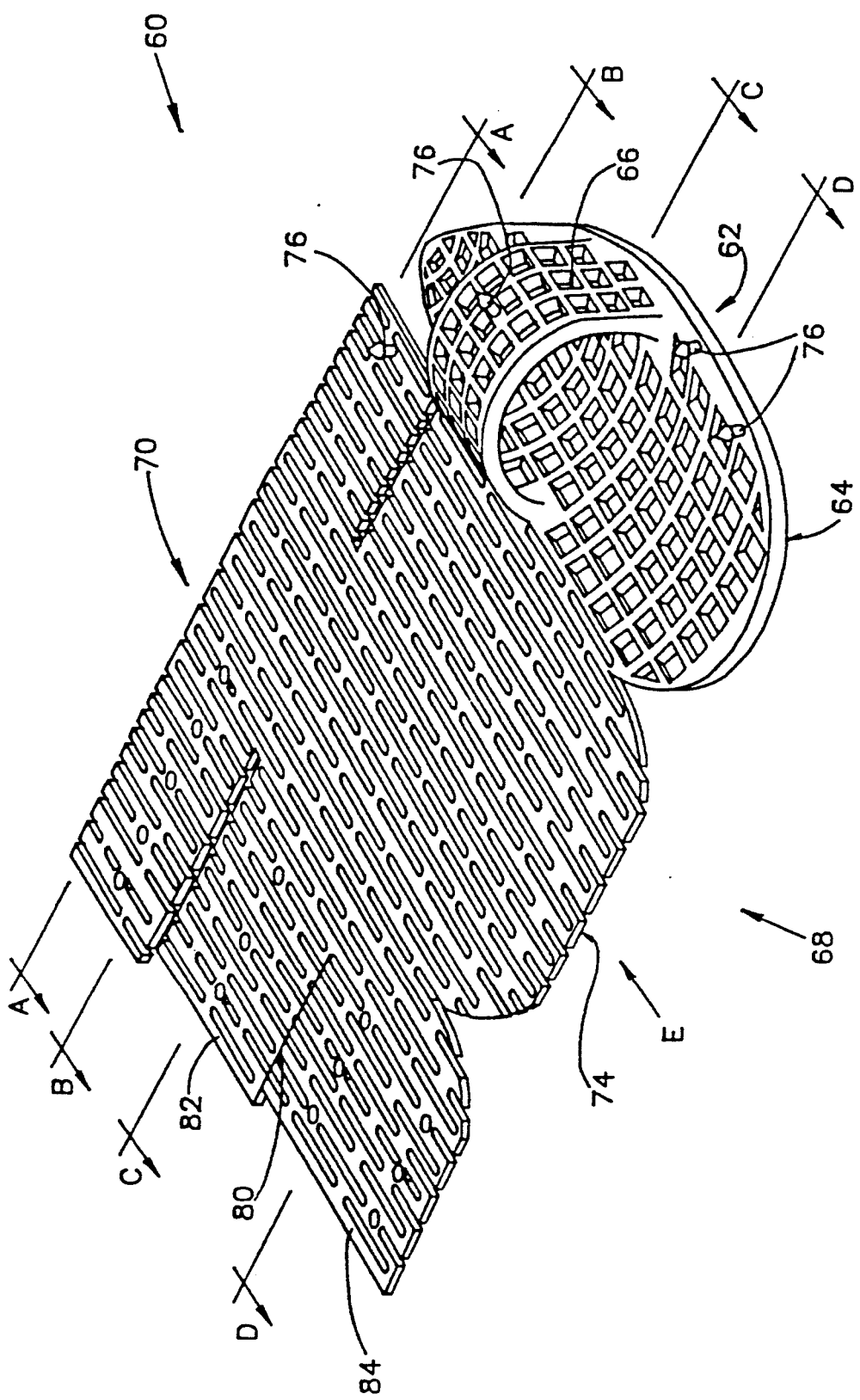
FIGS. 5 and 6 are pictorial illustrations of the front and back respectively of apparatus for applying a medicament transdermally to an animal ear constructed and operative in accordance with a preferred embodiment of the present invention.
Figure 6:
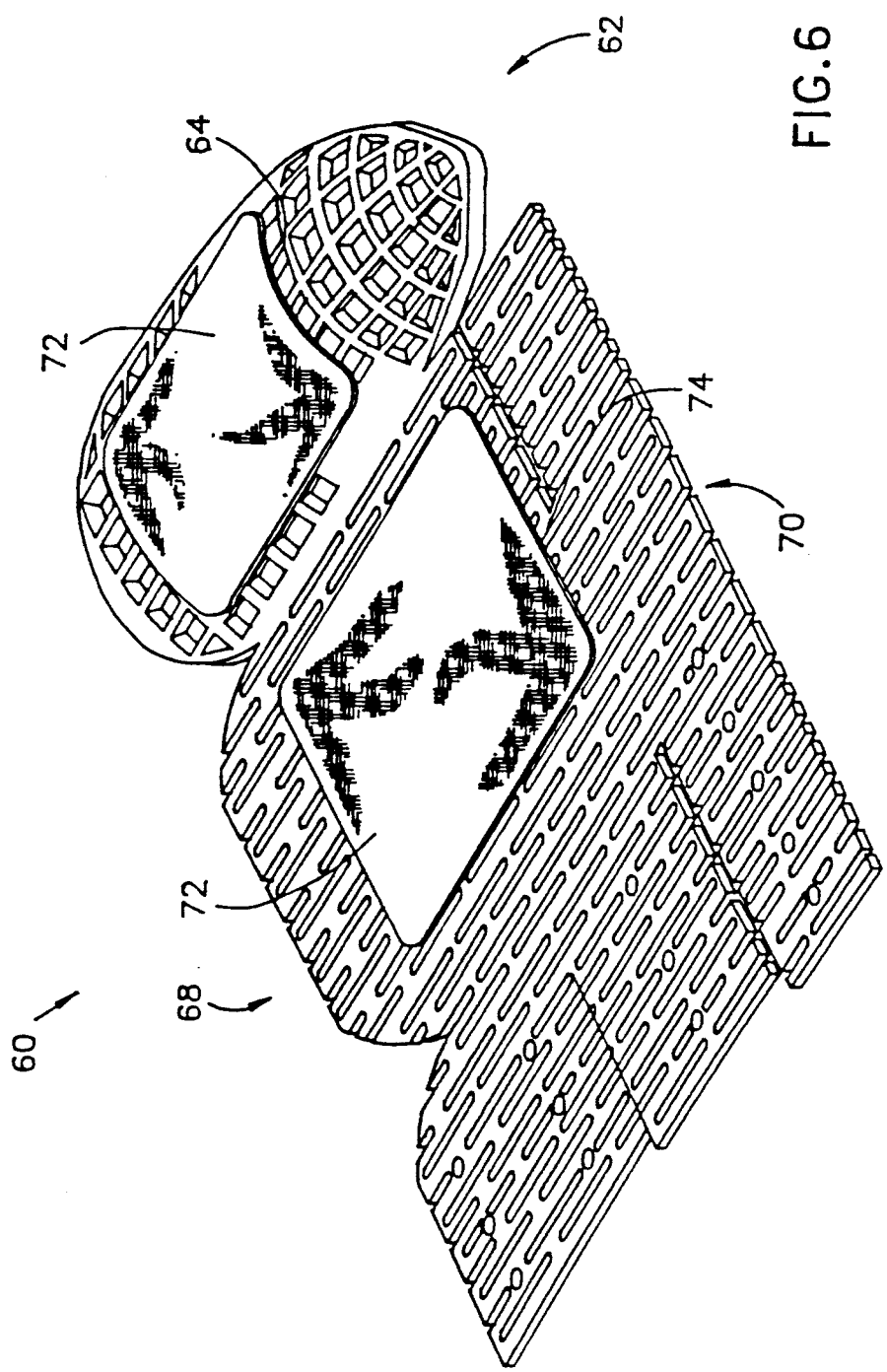

Reference is now made to FIG. 4, which shows a detail of a portion of the enclosure 10 having pores 50 which communicate either directly between the atmosphere and the animal ear or, as shown, via a porous medicament perforate solid support pad 52. The provision of pores is applicable equally to all of the embodiments illustrated in FIGS. 1A–3B.

It will be appreciated that all of the illustrated embodiments are only some examples of enclosures which may be employed in accordance with a preferred embodiment of the invention. The enclosure may be designed for a single use and thus be disposable or may be employed for multiple use.

The enclosures may be color or pattern encoded to provide a ready means of identification of the type and duration of treatment to the animal husbandry operative.

An example of the use of the invention in fertility synchronization is application of progesterone to ewes for 13 consecutive days by attachment of an enclosure as described above to the ewe's ear. Following the prescribed 13 days, the enclosure is removed and discarded. Mating should occur within 24 hours thereafter. Slaughter of the animal in any case should not take place less than 48 hours following removal of the enclosure.

An example of the use of the invention in the application of growth promoters is application of a combination of estradiol and progesterone to male cattle for 90 consecutive days by attachment of an enclosure as described above to the steer's ear. Following the prescribed 90 days, the enclosure is removed and discarded. Slaughter of the animal may take place no less than 5 days following removal of the enclosure.

An example of the use of the invention in the application of micronutritional supplements such as vitamins and trace elements is application of selenium (e.g. as dilsulfide) to cows for 90 consecutive days by attachment of an enclosure as described above to the cow's ear. Following the prescribed 90 days, the enclosure is removed and discarded. Application of the enclosure should be carried out at least 8 weeks before calving and terminated at the end of the weaning period.

Reference is now made to FIGS. 5–8 and 11A–11E, which illustrate the structure and mounting of a removable medicament-bearing enclosure constructed and operative in accordance with a preferred embodiment of the invention. The enclosure, indicated generally by reference numeral 60, comprises an inner ear portion 62 typically formed of a perforate web material of plastic, metal or any other suitable material.

The inner ear portion 62, serves to support the ear against deformation and includes a medicament-impregnated support holding curved portion 64, which lies against the inner surface of the animal ear and a bridge member 66 which supports the desired curvature of portion 64 and maintains spacing of the enclosure as desired. Associated with inner ear portion 62 and preferably integrally formed therewith is an outer ear wrap portion 68 and a collar portion 70. Preferably the inner ear portion 62 is formed of material which is somewhat more rigid than the material used for the outer ear wrap portion 68 and the collar portion 70.

The outer ear portion 68 is typically formed of a perforate web material of plastic, metal or any other suitable material which is somewhat stretchable. The collar portion 70 may be formed of identical material but should have limited stretchability. As noted above in earlier described embodiments, the medicament is provided on a perforate solid support (e.g. in the form of pads) 72 mounted on surface 64 of the inner ear engaging portion 62 and on surface 74 of outer ear wrap.

Figure 7:
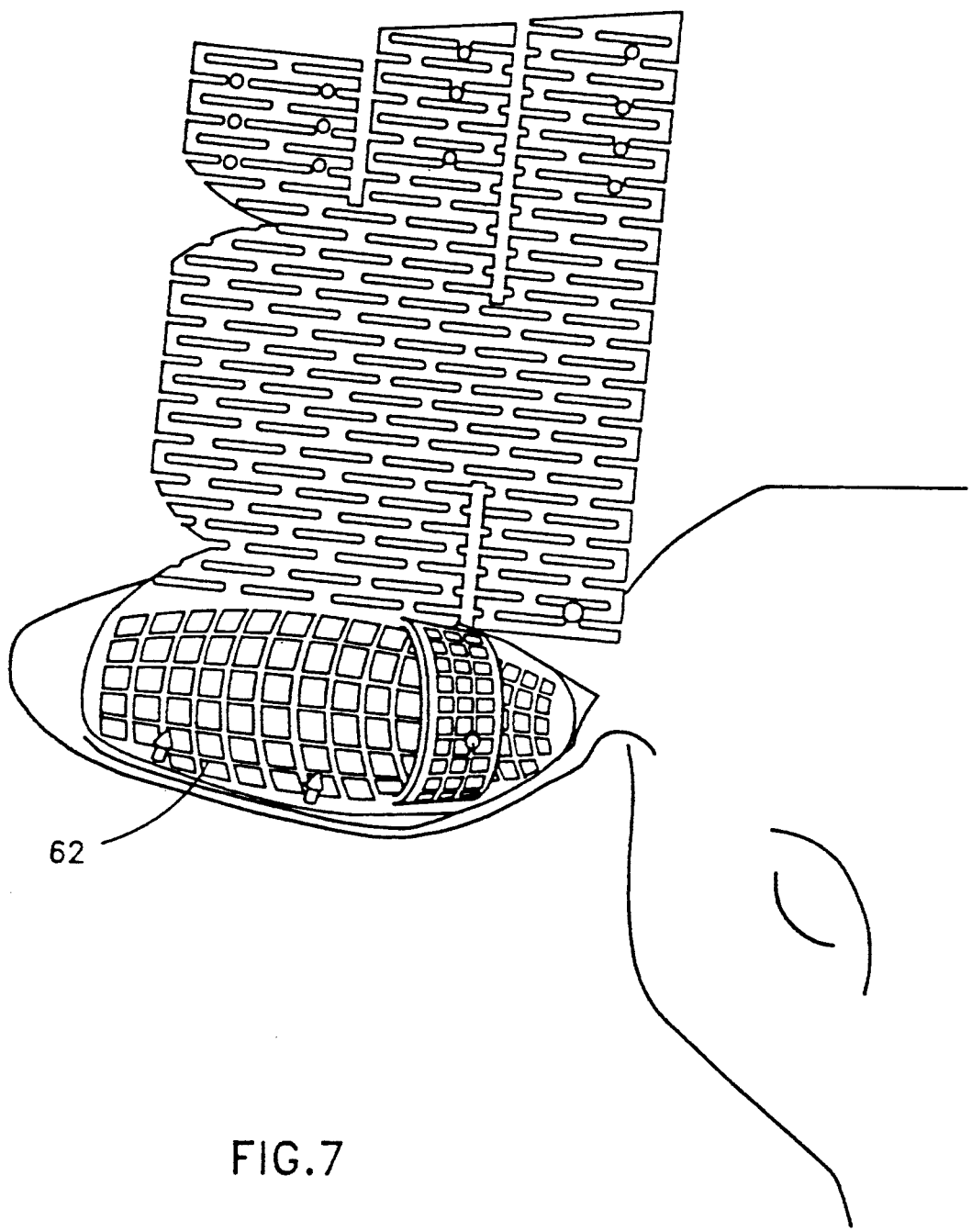
FIG. 7 is a pictorial illustration of the apparatus of FIGS. 5 and 6 partially mounted onto the ear of an animal.
Figure 8:
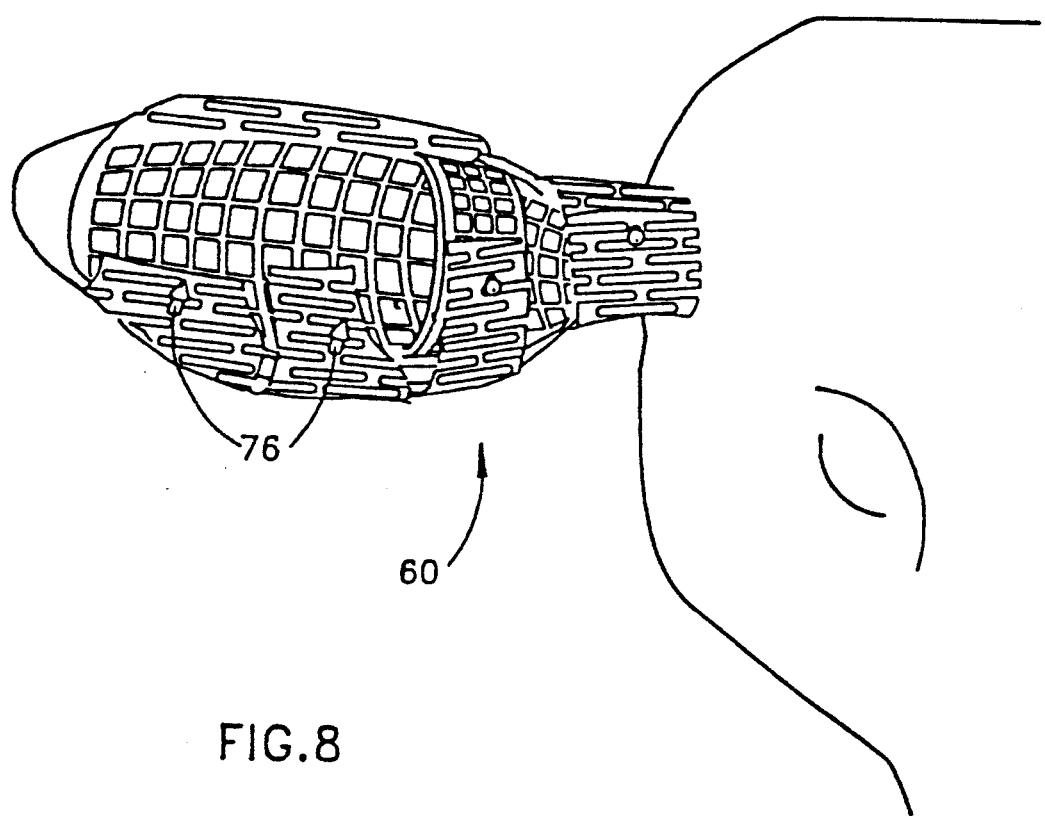
FIG. 8 is a pictorial illustration of the apparatus of FIGS. 5 and 6 fully mounted onto the ear of an animal.

FIG. 7 illustrates initial insertion of the inner ear engaging portion 62 into the ear of an animal and FIG. 8 illustrates complete fastening of the enclosure 60 onto the animal ear. It is noted that the collar portion is adjustably fastened relatively tightly about the narrow part of the ear closest to the head of the animal, in order to retain the enclosure on the ear. When it is desired to remove the enclosure, it is usually sufficient to unfasten the collar portion and to slide the enclosure off the ear.

In the illustrated embodiment, bayonet type fasteners 76 are employed, it being understood that any suitable type of fasteners may be employed. It is appreciated that in the illustrations the enclosure for a right ear is shown. The enclosure for the left ear is configured correspondingly.

It is noted that the fastening arrangement on the outer ear wrap portion is such that various differently sized ears may be readily accommodated by a universal enclosure. Different sized enclosures may however be required for full grown cows and calves, for example.

In the illustrated embodiment, the outer ear wrap portion includes a slit 80 between adjacent strap portions 82 and 84, in order to accommodate the curvature of the ear. Depending on the construction of the enclosure, this slit may be eliminated.

Figure 12:
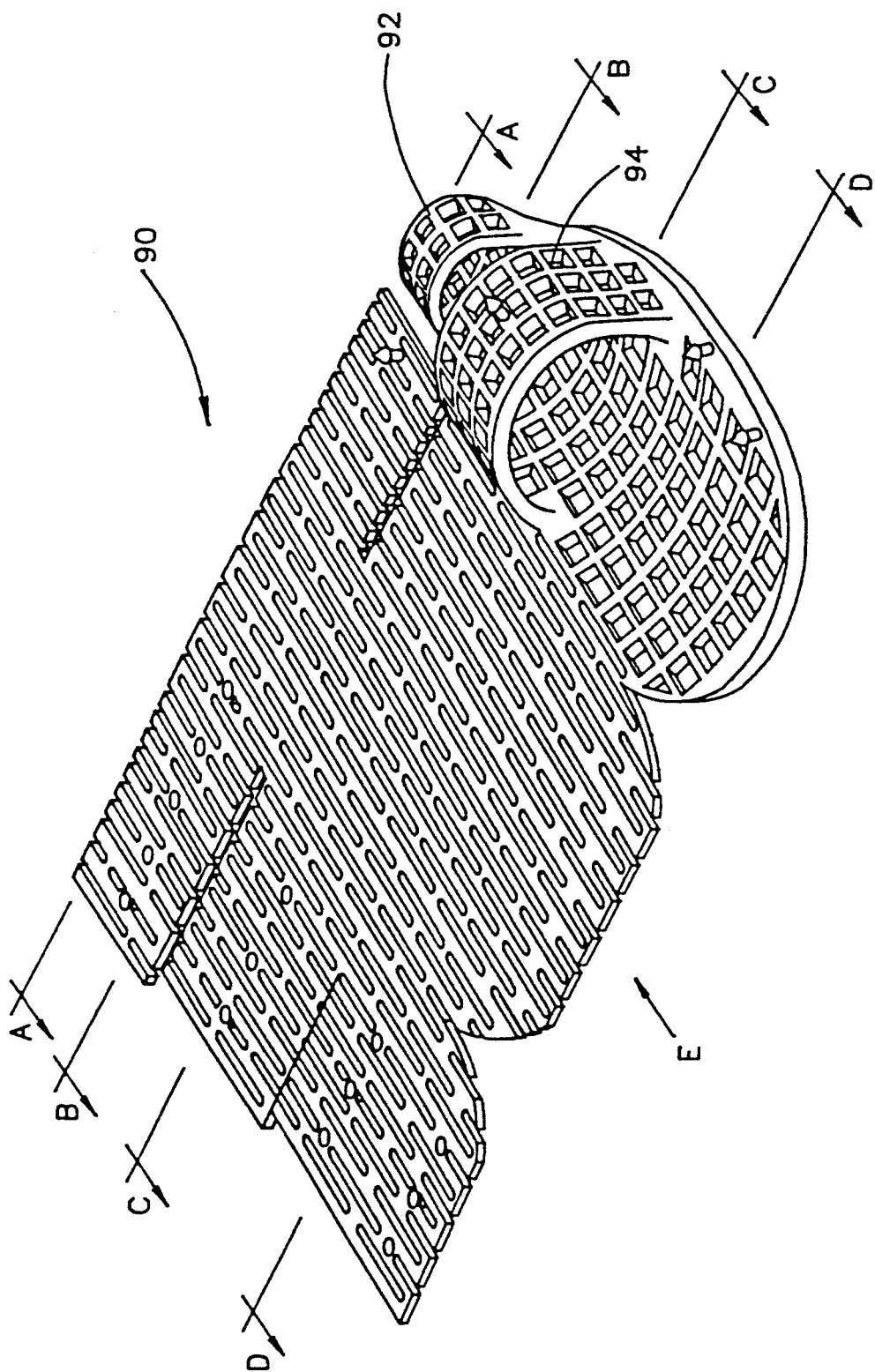
FIG. 12 is a pictorial illustration of the front of apparatus for applying a medicament transdermally to an animal ear constructed and operative in accordance with another preferred embodiment of the present invention.
Figure 13:
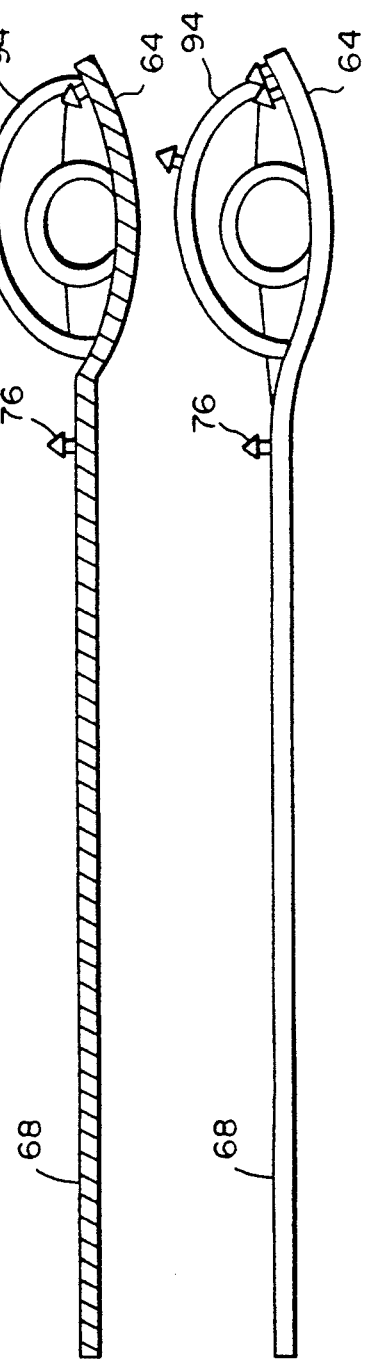
FIGS. 13A, 13B, 13C, 13D and 13E are sectional illustrations taken along lines A—A B—B C—C, D—D and in the direction E in FIG. 12.

An alternative embodiment of an enclosure, particularly suitable for use with sheep, goats and other small animals, is illustrated in FIG. 12. It is noted that enclosure 90 includes two bridge members 92 and 94 for enhanced support of the ear. FIGS. 13A, 13B, 13C, 13D and 13E are sectional illustrations taken along lines A—A, B—B, C—C, D—D and in the direction E in FIG. 12.

The invention will now be further illustrated by the following non-limiting Examples.

EXAMPLE I

Preparation of Medicament-Soybean Oil Mixture and Matrix Containing It

Soybean oil containing 400 mg.l. butylated hydroxytoluene (antioxidant) was heated at 38° C. and progesterone was added (to obtain (18.7 g./l. soybean oil), the mixture being thoroughly stirred for 15 minutes; the product was labelled "A". To product "A", there was added 17β-estradiol (a concentration of 10.7 g./l. soybean oil was obtained), the mixture again being thoroughly stirred for 15 minutes at 38° C.; the product was labelled "B". To product "B", there was added testosterone (a concentration of 23.6 g./l. soybean oil was obtained), the mixture again being thoroughly stirred for 15 minutes at 38° C.; the product was labelled "C".

Figure 14:
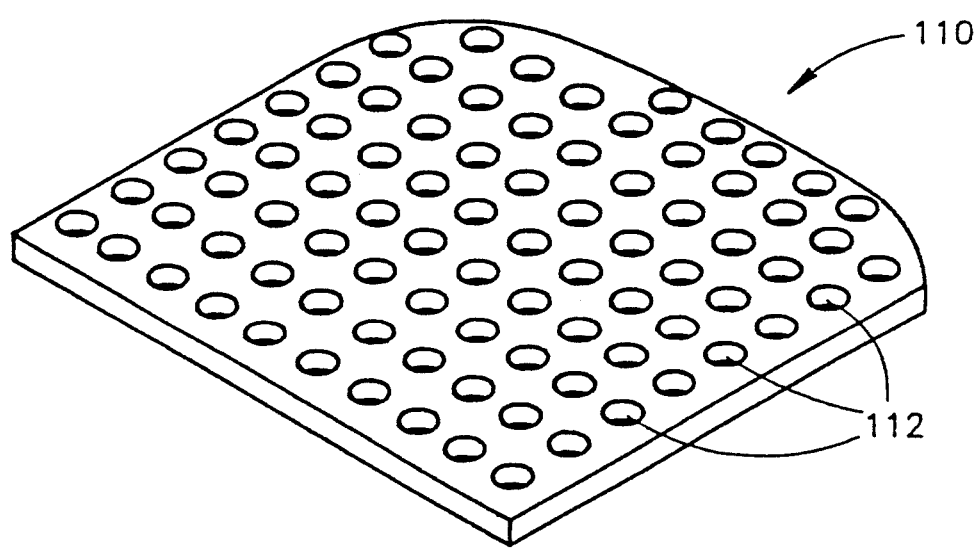
FIG. 14 is a pictorial illustration of an embodiment of the support useful in the present invention.

Products "A", "B" and "C" were used to impregnate pieces of "Spontex" (trade name) absorbent sponge (shown generally as 110 in FIG. 14), in which circular perforations 112 of diameter 4 mm had been made the centers of which were approximately 8 mm. apart. It will be appreciated that the particular support material used, as well as the nature and size of the perforations therein are merely illustrative. The matrices thus produced were utilized in the field trials described below.

EXAMPLE II

Transdermal Administration of Protesterone to Ewes

Introduction

The method in common use today to achieve synchronized oestrus in sheep, is to insert an impregnated sponge into the vagina and maintain it therein for 10–13 days. The sponge is typically impregnated with flugestone acetate or medroxyprogesterone acetate, which are absorbed in the vagina and which subject the ewe to a progestational action comparable with the luteal phase of the sexual cycle; this action ceases when the sponge is removed. The present example provides an evaluation of the technique of the invention, when used to artificially induce a progestational phase similar to that achieved by use of the impregnated vaginal sponge.

Method

The study was performed in May 1990 on five sexually mature ewes of mixed breeding (Table 1) of proven fertility, cycling normally during anoestrus and on an adequate nutritional diet. The ewes were part of a 200-sheep flock housed in a sheep shed in the central plain region of Israel.

TABLE 1

| | characteristics of the study animals | | |
|---|---|---|---|
| Ewe No. | Age* (years) | Weight* (kg.) | Breed |
| 1 | 3 | 40 | Merino/Finnish Landrace |
| 2 | 1.5 | 50 | Awasi/Finnish Landrace |
| 3 | 1.5 | 60 | Merino/Finnish Landrace |
| 4 | 3 | 70 | Merino/Awasi/Finnish Landrace |
| 5 | 2 | 50 | Merino/Finnish Landrace |

*approximate

Figure 9:
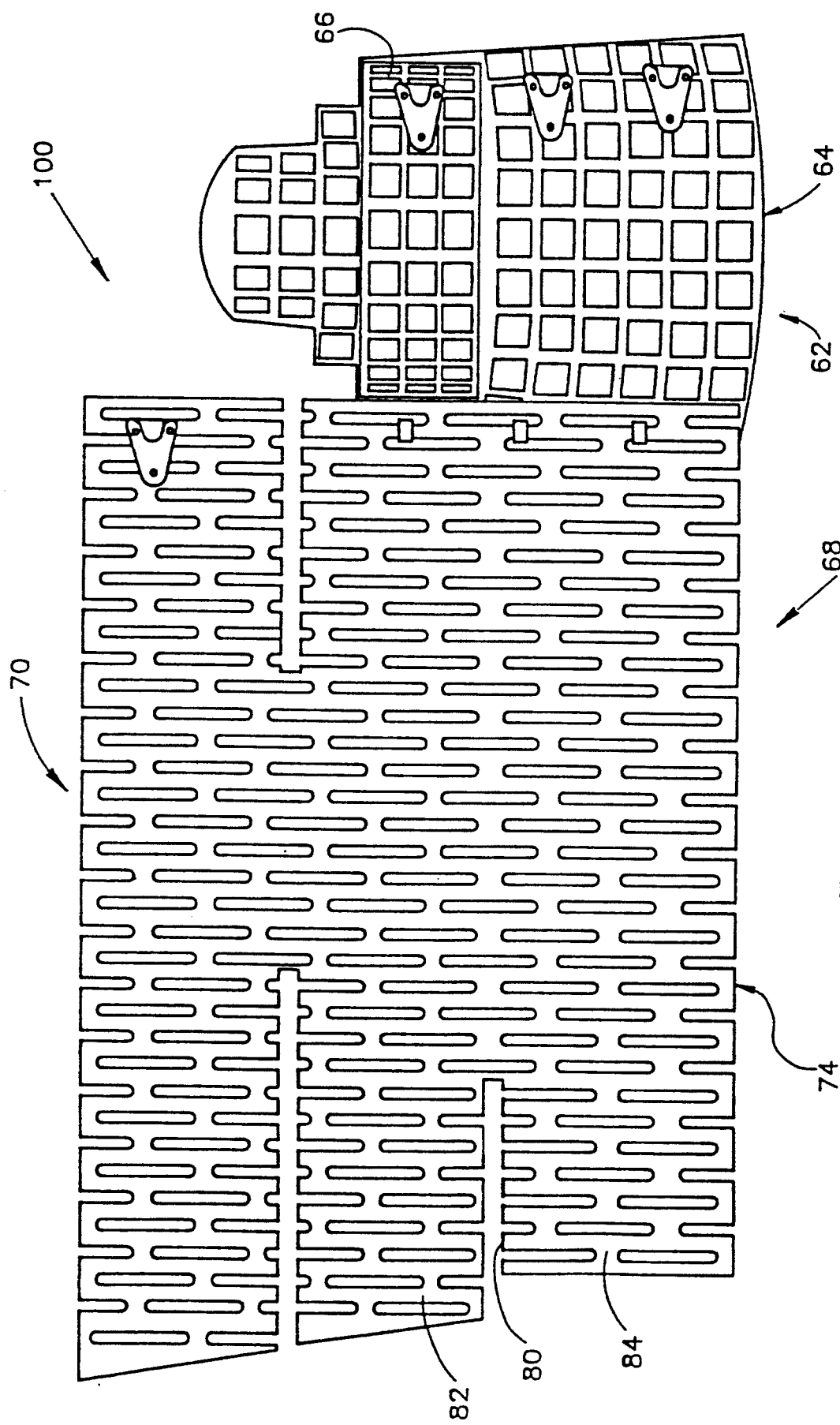
Figures 11A, 11C, 11D, 11E:
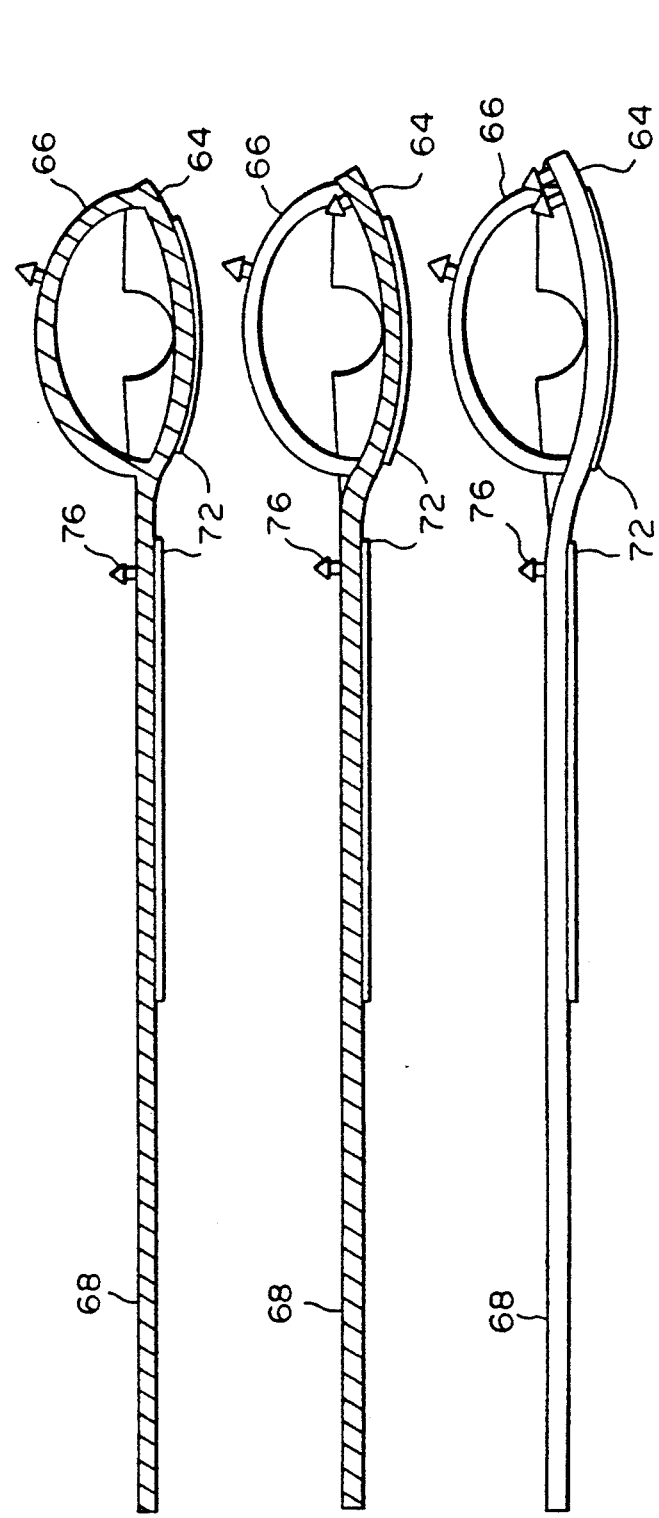

Enclosures 100 substantially as illustrated in FIGS. 9 and were employed. The elements of enclosure 100 are similar to those described in connection with FIGS. 5-8 and 11A-11E. Each ear device contained two similar drug matrices with respect to the amount of progesterone (each matrix containing approximately 276 mg. and of surface area approximately 60 cm.$^2$); the matrices were thus maintained in contact with the skin surface on each side of one only of the animal's ears. Each matrix contained approximately 15 ml. of product "A" (see Example I, above). The skin surfaces had not been shaved or otherwise prepared in any manner prior to attachment of the device containing the two drug matrices. The matrices were maintained on ewes nos. 1 and 3 for 10 consecutive days and on. ewes nos. 2, 4 and 5 for 13 consecutive days.

Prior to attaching the progesterone-containing devices, morning venous blood samples were taken from the jugular veins of each ewe on two consecutive days. Twelve hours after the second blood sample was taken the devices were attached. Twelve hours thereafter a morning blood sample was taken end then every morning except Saturdays until each device was removed. Twelve hours after each device was removed from ewes nos. 1 and 3 a morning blood sample was taken and then on the following two mornings; the devices were removed from the other ewes after 13 days. All five ewes were then injected with 600 i.u. PMSG (as a standard practice on this farm, at the end of synchronization treatment). Forty-eight hours after PMSG administration, blood samples were taken from all five ewes and 24 hours later the last blood sample was taken. Serum levels of progesterone were assayed in duplicates by solid-phase radioimmunoassay using D.P.C. Coat-A-Count methods. After the last blood sample was taken, circular biopsies (5 mm. diameter) were taken from each animal, 3 from the treated ear and 3 from the untreated ear (control). One biopsy was taken from the center of the ear and the other two from the periphery of the distal part of the ear.

The ear samples were preserved in 4% buffered formaldehyde saline. Transversal sections of the ear samples were prepared after hydration and embedding in paraffin wax. The sections were stained with hematoxylin and eosin, and were subsequently examined microscopically by a certified toxicological pathologist.

Results

Figure 15:
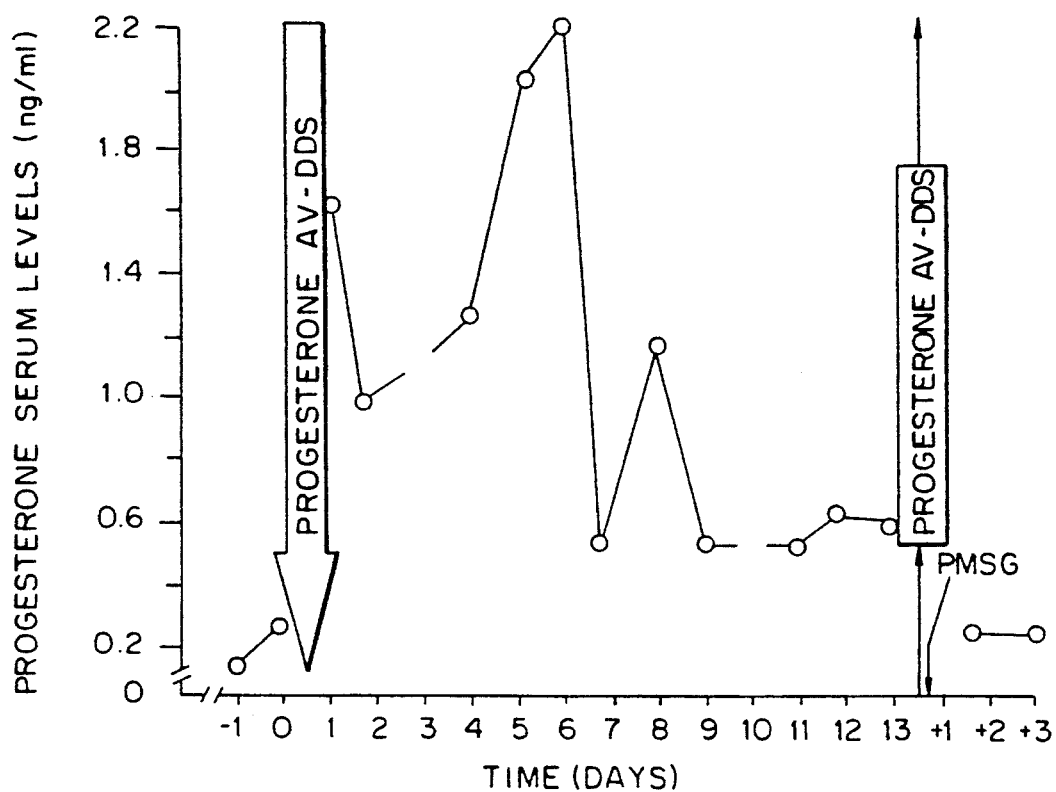
FIGS. 15, 16 and 17 depict respectively the variation of serum levels of 1, 2 or 3 medicaments over a time period, following their administration in accordance with embodiments of the present invention.

The device was readily mounted and removed, in seconds, as desired. Pretreatment progesterone serum levels averaged approximately 0.3 ng./ml. Progesterone serum levels from morning blood samples, taken 12 hours after the device was attached, were higher in all ewes than pretreatment values and ranged from 0.5 to 1.7 ng./ml., an average increase of 1 ng./ml. During the treatment period, progesterone serum levels ranged from 0.4 to 9.4 ng./ml. In all five ewes sustained release profiles were observed. Progesterone serum levels from morning samples taken 24 hours after the device was removed (10 days) from ewes 1 and 3 (first post-treatment blood sample ) were not different from pretreatment values and remained so for the next 7 days. Forty-eight hours after the device was removed from the other three ewes and the PMSG injected, the first blood sample was taken. Serum progesterone level from these samples as well as those taken 24 hours later averaged 0.3 ng./ml., i.e the same as the pretreatment levels. Mean progesterone serum levels during the study for the 3 ewes which were treated for 13 days are shown in FIG. 15.

The ears to which the devices had been attached showed light hair loss, slight scaling in three cases and slight diffuse acanthosis. Otherwise, there was evidence that observed light wounds were due to structural imperfections in the laboratory-made prototype device, which should be avoidable in a standard manufactured model.

EXAMPLE III

Transdermal Administration of Several Medicaments to Cattle from a Single Matrix Method Fertility and growth promoting agents were used in the present study, which was performed in May 1990 on six healthy Holstein calves kept in individual cages and fed normally; the location was a dairy farm in the central plain of Israel.

TABLE 2

| | characteristics of the study animals | | |
|---|---|---|---|
| Calf No. | Sex | Age (months) | Weight* (kg.) |
| 1 | M | 2 | 60 |
| 2 | M | 3 | 70 |
| 3 | M | 3 | 80 |
| 4 | M | 1.5 | 50 |
| 5 | M | 1 | 55 |
| 6 | F | 2 | 60 |

*approximate

Enclosures 100 substantially as illustrated in FIGS. 9 and 10, were employed. The elements of enclosure 100 are similar to those described in connection with FIGS. 5-8 and 11A-11E. Each ear device contained two similar drug matrices with respect to the amount of active agents and surface area (each approximately 60 cm.$^2$); the matrices were thus maintained in contact with the skin surface on each side of one only of the animal's ears. Each matrix contained approximately 10 ml. of product "B" or "C" (see Example I, above). The skin surfaces had not been shaved or otherwise prepared in any manner prior to attachment of the device containing the two drug matrices. The matrices applied to the five male calves contained in each matrix approximately 97 mg. 17$\beta$-estradiol and approximately 187 mg. progesterone. The matrices applied to the female calf contained in addition to estradiol and progesterone, approximately 230 mg. testosterone in each matrix. The drug matrices were maintained on the female calf (no. 6) for 6 consecutive days. On the male calves, the matrices were maintained on nos. 1 and 5 for 8 consecutive days, on nos. 2 and 3 for 13 consecutive days and on no. 4 for 16 consecutive days.

For 3 consecutive days prior to attaching the devices, morning venous blood samples were taken from the jugular veins of each calf. Twelve hours after the third blood sample was taken the devices were attached. Morning blood samples were then taken every morning except Saturdays; 12 hours after the last blood sample was taken, each device was removed. Twelve hours after each device was removed, a morning blood blood sample was taken and then again on each of the following three days.

Serum levels of progesterone, 17$\beta$-estradiol and testosterone (only assayed on the female calf) were determined in duplicates by solid-phase radioimmunoassay using D.P.C. Coat-A-Count methods. After the last blood sample was taken, six circular biopsies (5 mm. diameter) were taken from each animal; three from the treated ear and three from the untreated ear (control). One biopsy was taken from the center of the ear, one from the ear fold and one from the periphery of the distal part of the ear (opposite the ear fold).

The ear samples were preserved in 4% buffered formaldehyde saline. Transversal sections of the ear samples were prepared after hydration and embedding in paraffin wax. The sections were stained with hematoxylin and eosin, and were subsequently examined microscopically by a certified toxicological pathologist.

Results

The device was readily mounted and removed, in seconds, as desired.

Pretreatment estradiol (<10 pg./ml.) and progesterone (<0.1 ng./ml.) serum levels were less than the lower limit of detection in all six calves and the testosterone levels in the female calf at this period were also lower than the limit of detection (<0.1 ng./ml.). During the treatment, serum levels of progesterone, estradiol and testosterone (female only) were well within the limits of detection of the assay. Progesterone serum levels ranged from 0.1 to 2.2 ng./ml., estradiol from 13 to 1616 pg./ml. and testosterone from 2.6 to 10 ng./ml. In 5 of the 6 calves, serum levels of these agents were detected in the first blood sample which was taken 12 hours after the devices were attached. Serum levels of progesterone taken on the first blood sample 12 hours after the devices were removed were undetectable and in all the male calves the estradiol also. The testosterone serum level taken at this time from the female calf was 0.3 ng./ml.

Figure 16:
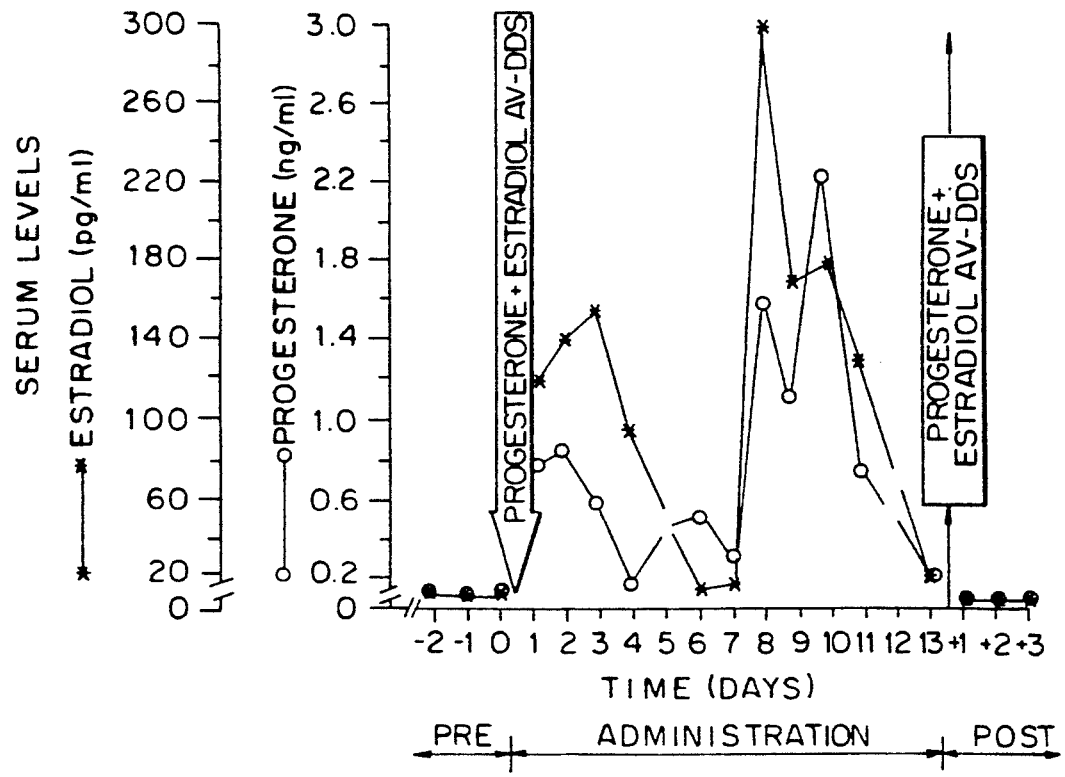
Figure 17:
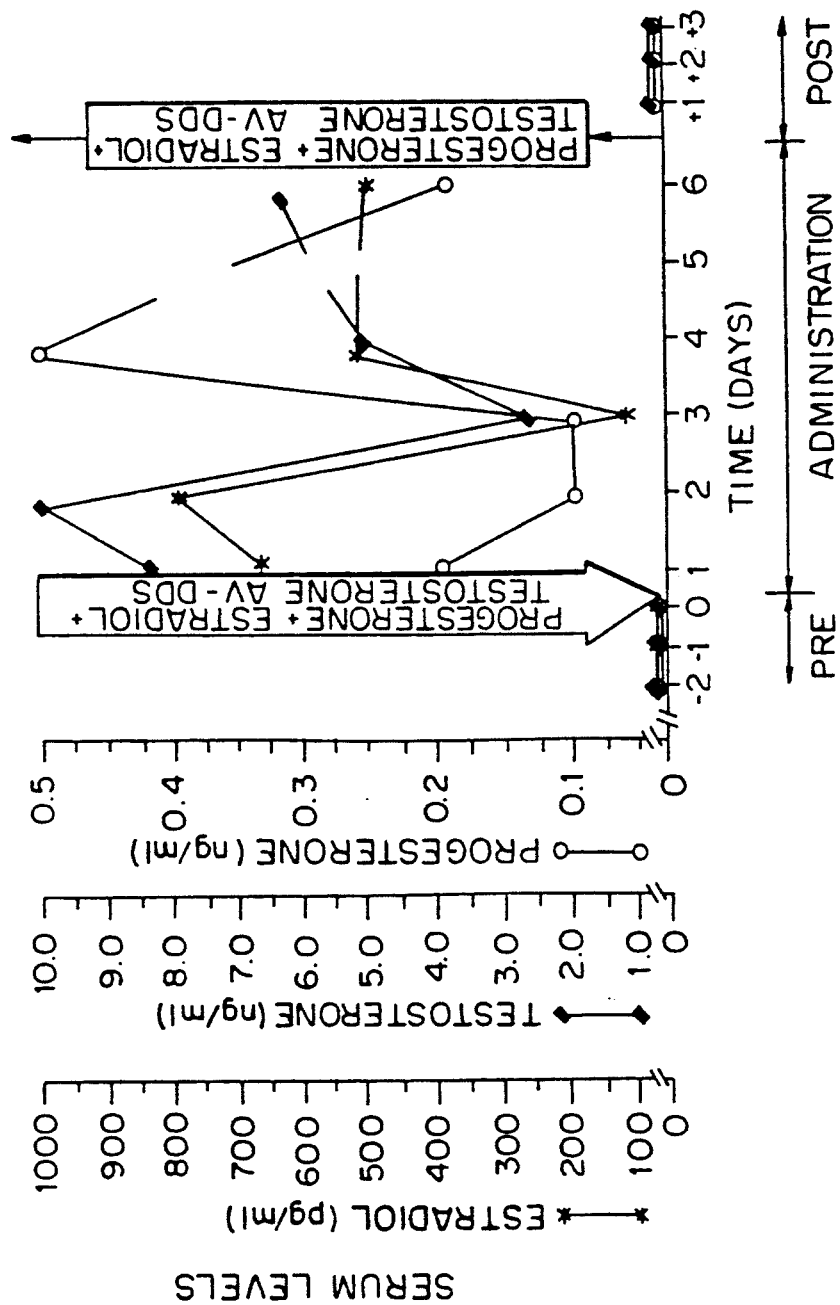

In two out of the six calves, levels of these medicaments following attachment of the device were sporadic, while in the other four, a sustained release profile was observed. Two examples of the sustained release profiles are presented in FIGS. 16 and 17.

The ears to which the devices had been attached showed moderate diffuse acanthosis in some cases. Otherwise, there was evidence that observed ulceration was due to structural imperfections in the laboratory-made prototype device, which should be avoidable in a standard manufactured model.

Conclusions

The results show that the utilized device enables several drugs to be simultaneously administered transdermally from a single matrix to cattle for an extended period of time under field conditions, while being compatible with the animal's skin. Further, drug blood levels can be rapidly achieved and can quickly return to pretreatment levels after the removal of the device. Also, the device can be easily and rapidly attached to initiate drug administration, and easily and quickly removed at the desired time to terminate drug administration, while preparation of the site of application is not required.

EXAMPLE IV

Animal Tests on Various Oils as Carriers for Transdermally Administered Medicaments Method The study was conducted on a farm located in the central plain region of Israel during September 1990. Male lambs of mixed breeding (Merino/Romanoff and Merino/Finnish Landrace) aged 4–5 months and weighing 45–55 kg. were fed hay and commercially available concentrated feed pellets once a day and had free access to water. Nine pharmaceutical compositions based on the following non-volatile oils, namely (1) peanut oil, (2) 90:10 almond oil/walnut oil admixture, (3) rapeseed oil, (4) soybean oil, (5) corn oil, (6) liquid coconut oil, (7) glycerol, (8) propylene glycol, and (9) paraffin oil were tested in groups of 3–4 lambs. Each of the nine compositions was prepared by mixing overnight at 38° C., 100 ml. oil with 500 mg. of 17$\beta$-estradiol as medicament and 40 mg. of butylated hydroxytoluene as antioxidant. The fatty acid content of the vegetable oils (1) to (6) and the estradiol concentration in each of oils (1) to (9), were determined, and are shown in Table 3, below.

TABLE 3

| Oil | Fatty Acid (%) | | | | | | Estradiol (mg./ml.) |
|---|---|---|---|---|---|---|---|
| | $C_{16:0}$ | $C_{16:1}$ | $C_{18:0}$ | $C_{18:1}$ | $C_{18:2}$ | $C_{18:3}$ | |
| (1)* | 10.57 | | 3.61 | 42.40 | 36.92 | 1.07 | 4.54 |
| (2) | 8.23 | | 2.24 | 21.01 | 55.95 | 12.57 | 4.94 |
| (3) | 5.39 | 0.21 | 1.54 | 58.46 | 22.83 | 11.57 | 5.34 |
| (4) | 10.48 | | 3.88 | 22.04 | 55.36 | 8.24 | 4.76 |
| (5) | 10.11 | | 1.85 | 28.49 | 58.38 | 1.17 | 5.48 |
| (6) ♦ | | | | | | | 4.10 |
| (7) | | | | | | | 4.91 |
| (8) | | | | | | | 5.12 |
| (9) | | | | | | | 6.34 |

*contained also 0.54% $C_{20:0}$

♦ contained 54.2% $C_{8:0}$, 45.1% $C_{10:0}$, Q.80% $C_{12:0}$

Experiments were conducted with preliminary prototype ear devices. To each such device, a matrix was attached. The matrix was made up of 4 mm. thick Spontex ® absorbent sponge in which circular perforations of 4 mm. diameter had been made, the centers of the circles being approximately 8 mm. apart. The surface area of the matrix was 110 cm.$^2$ (55 cm$^2$ surfaces covering the outer and inner surfaces of the ear, respectively). This matrix was impregnated with 16 ml. of the composition under test, and the system (ear device with impregnated matrix attached), which weighed approximately 50 g., was mounted on the lamb's ear. The skin surfaces of the ear were not shaved or prepared in any manner prior to mounting of the device. The systems were removed from the lamb's ear after four consecutive days.

Medicament penetration of the skin was assessed by determining 17$\beta$-estradiol concentration (by solid phase radioimmunoassay) in the serum at intervals over period of the investigation. In the morning (0700–0800) venous blood samples were taken from the Jugular vein on three consecutive days before mounting the device; in all animals except two, it was found that the serum did not contain a measurable quantity of 17$\beta$-estradiol (<10 pg./ml.), the exceptions contained 12.3 and 17.1 pg./ml. The device was then mounted and a blood sample was taken after two hours and on consecutive mornings following attachment of the device. After four days of attachment, the device was removed. Morning blood samples were taken on the three consecutive days following removal of the device.

After the device was removed from the lamb's ear, the treatment site and the whole ear were examined. Following physical examination, samples were taken from the ear for biopsy.

Results of these tests are summarized in Table 4.

TABLE 4

| Oil | no. of animals/ result of examination | Estradiol serum concentration after | | | Estradiol serum concentration post-administration | | |
|---|---|---|---|---|---|---|---|
| | | 2 hrs | 1 day | 4 days | +1 | +2 | +3(days) |
| (1) | 4§ | d | c+ | d | 0 | 0 | 0 |
| (2) | 3■ | d | c | c+ | 0 | 0 | 0 |
| (3) | 4■ | c− | c | 0 | 0− | 0− | 0− |
| (4) | 3■ | c− | e | c− | a− | 0− | 0− |
| (5) | 3§ | c− | b | c− | a | c− | 0 |
| (6) | 3♦ | g | f | f− | 0 | 0 | 0− |
| (7) | 4♦ | 0 | a− | 0 | a− | 0 | 0− |
| (8) | 4♦ | f | f− | c | c− | a− | 0− |
| (9) | 4♦ | e− | a− | 0 | 0− | 0− | 0− |

KEY TO TABLE 4:
Estradiol serum concentration
0— no animals had significant amounts > 20 pg./ml.
0 no more than ¼ animals had significant amounts > 20 pg./ml.
a— at least 2/4 animals had over 19.5 pg./ml.
a all animals had over 19.5 pg./ml.
b all animals had over 28 pg./ml.
c— at least ¾ animals had at least 30 pg./ml.
c all animals had over 38 pg./ml.
c+ all animals had over 42 pg./ml.
d all animals had over 57 pg./ml.
e— ¾ animals had over 70 pg./ml.
e all animals had over 67 pg./ml.
f— all animals had over 92 pg./ml.
f all animals had over 145 pg./ml.
g all animals had over 300 pg./ml.
Physical observation of ear, post administration
§ no abnormality detected in at least 50% of animals
■ no more than slight/moderate swelling in at least ¾ animals
♦ ulceration, encrustation or moderate/severe swelling in at least ¾ animals Discussion of Results As already pointed out, the ear devices were prototypes. Therefore, this discussion will be subject to the reservations that they are to be regarded as preliminary results which may point to the need for further investigations, and are intended principally to convey whether the substances tested as carriers are likely to be effective in transporting medicaments through the skin, and to obtain an indication of skin compatability of these substances. Subject to these reservations, the following trends may be observed with regard to transdermal transport of the estradiol to the serum.

Two hours after administration, the descending order of carrier efficacy was as follows: 6>8>9>1,2>3-5>7, and in all cases except that of glycerol, there was a significantly increased concentration of estradiol in the serum of the test animal, liquid coconut oil being the most effective carrier, followed by propylene glycol.

At one day after administration, the descending order had become: 6>8>4>1>2,3>5>7,9; at this stage, soybean oil, in third place after liquid coconut oil and propylene glycol, had become more effective than at the two-hour stage, and the initial efficacy of paraffin oil had fallen away.

At four days after administration, the descending order had become: 6>1>2>8>4 5>3,7 9; at this stage, rapeseed oil had joined glycerol and paraffin oil as being apparently relatively ineffective, while peanut, oil and to a lesser extent the 90:10 almond/walnut oils admixture, had improved their performance as medicament carriers.

As may be seen from Table 4, in most cases the medicament did not persist in the animal's serum, once the device was removed, a result which was not entirely surprising. Exceptionally, however, the medicament carried transdermally by corn oil and by propylene glycol, maintained a significant presence in the serum in the 1-2 day period following removal of the device.

As regards the effect of administration on the test animal's ear, it is believed that the sporadic findings of ulceration in the case of liquid coconut oil and propylene glycol were most probably caused by accidental traumatic injury (i.e. by scratching), and should therefore not adversely effect the utility of these particularly effective medicament carriers. In general terms, it is concluded that vegetable oils and propylene glycol are particularly effective as carriers for medicaments to be administered transdermally, but that glycerol and paraffin oil might nevertheless find some application for this purpose.

Insofar as it is believed that the screening method employed in this Example is an embodiment of a more general method which possesses both novelty and inventivity, there is further provided in accordance with the present invention a method for testing the potential viability for transdermal administration in veterinary applications of a mixture of a preselected medicament with a preselected carrier for the medicament, which method comprises applying non-adhesively to the skin of an animal, for a preselected time period, a matrix which comprises a porous, absorbent perforate solid support, having the mixture absorbed thereon, and assaying the blood levels in the animal of the medicament over the preselected time period.

EXAMPLE V

Relative Medicament Penetration through the Inner and Outer Ear Skin Surfaces of Male Calves In the specific examples herein of transdermal administration of compositions in accordance with the invention, a device (sometimes referred to as AV-DDS) has been used in which the medicament in question was applied to both inner and outer skin surface of either one or both ears of animals. The present study is intended to examine the relative penetration of medicament through these two different skin surfaces.

Method

This study was conducted on a dairy farm located in the central plain region of Israel during August, 1990. It was carried out on five healthy male Holstein calves having the following ages and weights: #245, 2.5 months, ~60 kg.; #604, 2.5 months, ~70 kg.; #621, 2.5 months, ~70 kg.; #298, 2.5 months, ~75 kg.; and #307, 3 months, ~90 kg. Each calf was kept in an individual cage, but was fed and otherwise treated normally. Experiments were conducted with laboratory-made ear device prototypes and preliminary laboratory-made dosage forms. To each ear device, there were attached one dosage form to be applied to one surface of the animal's ear, and a different dosage form to be applied simultaneously to the other surface of the same ear. There was no contact between the different dosage forms. The skin surfaces of the ear were not shaved or otherwise prepared in any manner, prior to attachment of the device to the animal's ear.

The matrix for each dosage form was made of a 4 mm. thick Spontex ® absorbent sponge in which circular perforations of 4 mm. diameter were made, the centers of which were approximately 8 mm. apart. The surface area of each matrix was 60 cm.$^2$, and was applied to one surface of the ear only, as stated. Each matrix was impregnated prior to attachment with 11 ml. of either a mixture of 25 mg./ml. progesterone (Sigma) in soybean oil so as to contain 275 mg. progesterone, or 15 mg./ml. 17β-estradiol (Sigma) in soybean oil so as to contain 165 mg. estradiol. The AV-DDS devices in which the impregnated matrices were incorporated were maintained on each animal for 2 consecutive days. Morning (0700–0800) venous blood samples (10 ml.) were taken from the Jugular vein of each animal before administration of the medicament on either 1 or 2 (consecutive) days, immediately prior to attachment of the device and then at 1 and 2 days thereafter. Serum concentrations of the medicaments were assayed in duplicates by solid phase radioimmunoassay.

Experiment 1

The device mounted on calves #245, #604 and #621 maintained the progesterone dosage form in direct contact with the inner ear surface and the estradiol dosage form in direct contact with the outer surface of the same ear.

The device mounted on calves #298, and #307 maintained the progesterone dosage form in direct contact with the outer ear surface and the estradiol dosage form in direct contact with the inner surface of the same ear.

Experiment 2

After it had been determined that the animals' serum levels of the medicaments had the same values as before Experiment 1, the device was mounted on calf #621 and maintained 11 ml. soybean oil (without medicament) in direct contact with the inner ear surface and the estradiol dosage form in direct contact with the outer surface of the same ear, while the device mounted on calf #298 maintained 11 ml. soybean oil (without medicament) in direct contact with the outer ear surface and the progesterone dosage form in direct contact with the inner surface of the same ear.

Two devices were mounted on calf #307 one on each ear. The device mounted on the left ear maintained 11 ml. soybean oil (without medicament) in direct contact with the outer surface of that ear and the estradiol dosage form in direct contact with the inner surface of the same ear, while the device mounted on the right ear maintained 11 ml. soybean oil (without medicament) in direct contact with the inner surface of that ear and the progesterone dosage form in direct contact with the outer surface of the same ear.

Results

The results are shown in Table 5 below. It is noted that pretreatment serum levels of progesterone (<0.1 ng./ml.) and estradiol (<10 pg./ml.) were lower than the limit of detection in all the calves, in both experiments.

In Experiment 1, progesterone was detected in all the blood samples taken during the treatment period with the exception of calf #298, in which progesterone was detected on day 2 and not on day 1. Estradiol was detected in all the blood samples taken during the treatment period.

In Experiment 2, progesterone was detected in all the blood samples taken during the treatment period from calves #298 and #307. Estradiol was detected in all the blood samples taken from calves #621 and #307 during the treatment period.

Conclusion

It may be noted from the results tabulated below, that there was no significant difference between the penetration of either medicament, through either the hairy outer skin surface of the ear, or the waxy inner skin surface of the ear.

TABLE 5

| Medicament | Ear Surface | Calf # | Medicament Serum Concentration* Day No. | | | | |
|---|---|---|---|---|---|---|---|
| | | | −2 | −1 | 0 | 1 | 2 |
| progesterone | inner | 245 | <0.1 | <0.1 | <0.1 | 0.42 | 0.69 |
| (Expt. 1) | | 604 | <0.1 | <0.1 | <0.1 | 0.12 | 0.42 |
| | | 621 | <0.1 | <0.1 | <0.1 | 0.95 | 0.44 |
| progesterone | outer | 298 | <0.1 | <0.1 | <0.1 | <0.1 | 0.16 |
| (Expt. 1) | | 307 | <0.1 | <0.1 | <0.1 | 0.37 | 0.41 |
| estradiol | outer | 245 | <10 | <10 | <10 | 213.6 | 209.8 |
| (Expt. 1) | | 604 | <10 | <10 | <10 | 110.3 | 250.6 |
| | | 621 | <10 | <10 | <10 | 208.1 | 175.9 |
| extradiol | inner | 298 | <10 | <10 | <10 | 214.6 | 124.4 |
| (Expt. 1) | | 307 | <10 | <10 | <10 | 319.6 | 85.2 |
| progesterone | outer(R) | 307 | — | <0.1 | <0.1 | 0.2 | 0.3 |
| (Expt. 2) | inner(R) | 298 | — | <0.1 | <0.1 | 0.4 | 0.2 |
| estradiol | outer(R) | 621 | — | <10 | <10 | 187.0 | 44.0 |
| (Expt. 2) | inner(L) | 307 | — | ·<10 | <10 | 23.0 | 158.6 |

*progesterone, ng./ml., estradiol pg./ml.

EXAMPLE VI

Continuation Transdermal Administration of Levamisole to Sheep

Introduction

Levamisole is widely used as an anthelmintic, and possesses a broad spectrum of activity against adult and immature gastrointestinal helminths and lungworms. It is commonly used in cattle, sheep, swine and goats. It is normally administered orally or by deep intramuscular injection or by subcutaneous injection as the hydrochloride; generally, these routes are considered equivalent in efficacy. Topical preparations for cattle have recently been introduced onto the market.

Levamisole is a stimulant of Nematode ganglia, leading to neuromuscular paralysis of the parasites. Because of its mechanism of action, the peak blood concentration is more relevant to its antiparasitic activity than the duration of concentration.

In cattle, peak blood levels of levamisole occur in <1 hour after subcutaneous administration. These concentrations then decline rapidly and 90% of the total dosage is excreted in 24 hours, largely in the urine.

Since levamisole acts on the roundworm nervous system, it is not ovicidal. This, coupled with the fact that levamisole is rapidly excreted after administration, can therefore only offer limited protection against reinfestation when administered in the available modes of administration.

It would therefore be advantageous if the anthelmintic action of levamisole could be prolonged after a single administration and thus provide better protection with respect to reinfestation.

The purpose of the present study is to determine whether the incorporation of levamisole in the transdermal administration system and compositions according to the invention can achieve levamisole blood levels which are sustained for a longer period than those achieved by the current modes of administration.

Method

The study was conducted on a farm located in the central plain region of Israel during October 1990. Male lambs of mixed breeding (Merino/Romanoff and Merino/Finnish Landrace) aged 5–6 months and weighing 45–55 kg. were fed hay and commercially available concentrated feed pellets once a day and had free access to water. The lambs were randomly divided into groups I (3 lambs), II (2 lambs) and III (3 lambs), each group being housed in a separate pen.

Venous blood samples (10 ml.) were taken from the jugular vein of each lamb before treatment and then 1, 2 and 4 hours after commencement of treatment. Blood samples were then taken every morning (0700–0800) for the next four days in groups I and III, and for eight days (except day 3) in group II.

Group I was treated with a single 3 ml. intramuscular injection of 225 mg. levamisole in the form of a 7.5% solution (Caliermisol) marketed by Laboratorios Caller S.A. (Barcelona, Spain). Groups II and III were treated with the AV-DDS device containing the different levamisole dosage forms. In these experiments, preliminary prototype ear devices produced in a pilot production facility were used. To each such device a matrix was attached. The matrix was made up of 4 mm. thick Spontex ® absorbent sponge in which circular perforations of 4 mm. diameter had been made, the centers of the circles being approximately 8 mm. apart. The surface area of the matrix was 110 cm.$^2$ (55 cm$^2$ surfaces covering the outer and inner surfaces of the ear, respectively).

A mixture of 20 g. levamisole-HCl, 25 ml. liquid coconut oil and 100 ml. soybean oil was stirred at 37° C. overnight. In group II (dosage form "A") each matrix was impregnated with 16 ml. of the levamisole mixture and the system (ear device with impregnated matrix attached) weighed ~50 g. In group III (dosage form "B") each matrix was first impregnated with 8 ml. sunflower seed oil and then with 16 ml. of the levamisole mixture; the system weighed ~57 g. The total amount of levamisole contained in each dosage form in groups II and III was 2560 mg. The skin surfaces of the ear were not shaved or prepared in any manner prior to mounting of the system (AV-DDS). Levamisole skin penetration was assessed by determining the concentration of levamisole in the serum by a gas chromatographic method; the limit of detection of the assay was 0.05 µg. levamisole/ml.

Results

Figure 18:
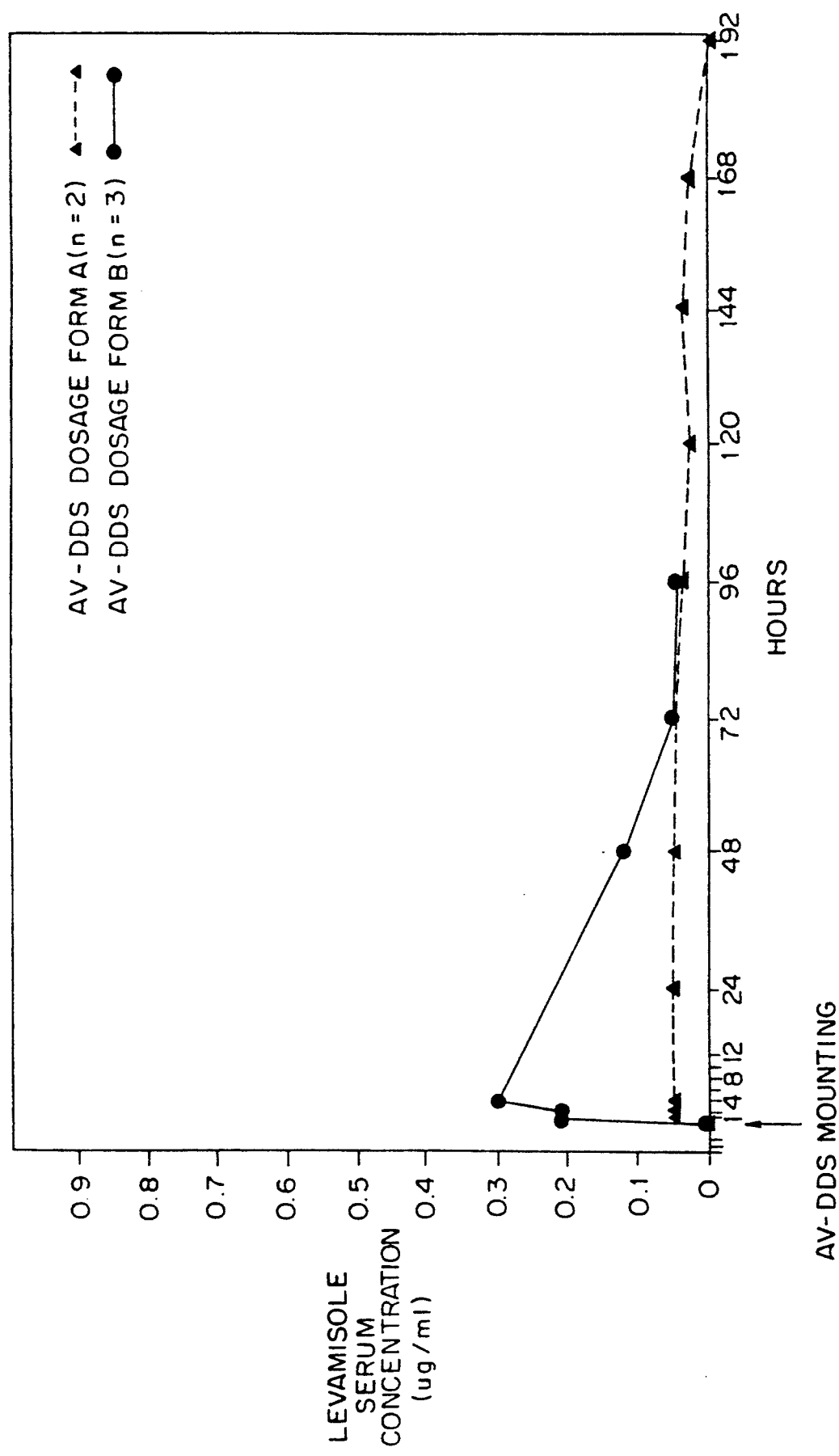
FIG. 18 depicts the variation of levamisole serum levels with time, following administration in accordance with embodiments of the present invention.
Figure 19:
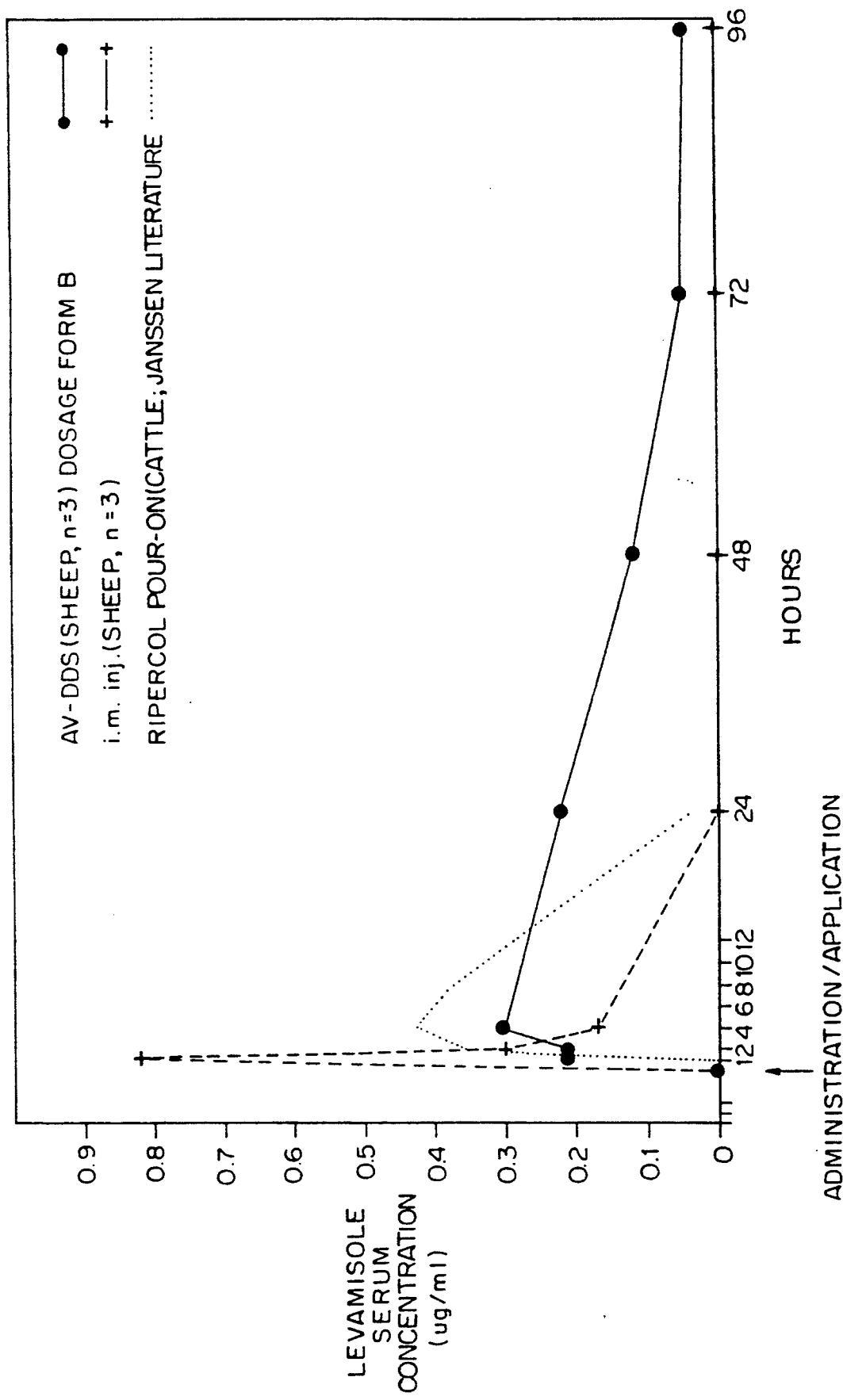
FIG. 19 is similar to FIG. 18, but compares an embodiment of the present invention with prior art techniques.

Table 6 shows the amount of levamisole in serum for groups I, II and III, at the indicated time intervals after administration. Prior to administration, no levamisole was detected. These results are depicted graphically in FIG. 18 (group I) and in FIG. 19 (groups II and III).

TABLE 6

| Group | no. of animals | Levamisole serum concentration (µg./ml.) after | | | | | | |
|---|---|---|---|---|---|---|---|---|
| | | 1 hr | 2 hrs | 4 hrs | 24 hrs | 4 days | 6 days | 8 days |
| I* | 3 | 0.8 | 0.3 | 0.17 | 0 | 0 | | |
| II | 2 | 0.05 | | | 0.05 | 0.05 | 0.05 | 0 |
| III | 3 | 0.2 | 0.2 | 0.3 | 0.2 | 0.05 | | |
| ** | | 0 | | | 0.43 | 0.04 | | |

*225 mg. levamisole administered intramuscularly
**Ripercol(R) (Janssen) pour-on preparation, the data shown is deduced from the graph in promotional literature Discussion of Results Rapid and sustained levamisole serum concentrations were achieved with both dosage forms "A" and "B", although the concentration in the case of "A" was low. A more sustained release of levamisole was obtained with dosage form "B" than with the pour-on preparation, though at a somewhat lower concentration than the peak level of the pour-on preparation. As regards rate of penetration of levamisole, transdermal administration according to the present invention resembles an intramuscular injection, but in terms of peak serum concentrations, dosage form "B" resembles the pour-on preparation. However, both transdermally administered dosage forms "A" and "B", are unique in that the period of sustained blood levels is measured in days rather than hours, as compared with both the intramuscular injection and the pour-on preparation, thus providing improved protection against reinfestation. Also, since the present mode of administration is external, treatment can be terminated at any time simply by removal of the system.

EXAMPLE VII

Continuous Transdermal Administration of Ivermectin to Sheep

Introduction

Ivermectin a semisynthetic macrocyclic lactone, introduced in 1981, belongs to a group of broad spectrum antiparasitics which have been widely used in the treatment of endo- and ecto-parasites in sheep, horses, swine and cattle. It is a mixture of homologs comprising not less than 80% of 22,23-dihydroavermectin $B_{1a}$ and not more than 20% of 22,23-dihydroavermectin $B_{1b}$, although there is no difference in the antiparasitic activity of the two.

Ivermectin is absorbed systematically after oral or subcutaneous administration, but is absorbed to a greater degree when given subcutaneously. The route of administration and the nature of the formulation employed affect its disposition profile. Most of the administered dose of Ivermectin is excreted in the feces, the remainder in the urine. Drug residues were reported to be higher in the liver and in fat than in other edible tissues, and the major component of the residues was unaltered Ivermectin.

As with other anthelmintics, efficacy is profoundly affected by both the potency of the drug and its residence time within the treated animal, or its kinetic profile. Several modes of drug administration, unique in terms of applicability only in animal health and restricted mainly to cattle, have been developed to increase the residence time of the active drug in the treated animal. These include unique injectable formulations, pour-on preparations and ruminal boluses. While such techniques prolong the residence time of the drug after a single application (thus increasing efficacy), they simultaneously possess the disadvantage that longer residence time necessitates a longer withdrawal period before milk or meat from the treated animals can be used for human consumption. Withdrawal time cannot be shortened with these techniques, since such systems are placed within the animal, and once administration commences, it must run its full course and cannot be terminated at will.

On the other hand, the AV-DDS system has been developed to achieve, both the features of sustained drug levels and the ability to terminate treatment when desired. This system is an external, non-invasive system which can be readily mounted on the animal's ear, can be as readily removed when desired, and also enables the animals undergoing treatment to be visually identified. The system includes two components, namely, the device itself (which maintains the medicament dosage in direct contact with the skin for the desired duration of treatment) and the transdermal dosage form attached thereto.

Method

The study was conducted on a farm located in the central plain region of Israel during November 1990, on 9 lambs of mixed breeding (Merino/Cambridge) aged approximately 4 months and weighing 30–35 kg. The lambs were divided into three experimental groups (3 per group), each group being kept in separate pens; they were fed once a day with commercially available concentrated feed pellets, hay and water being available ad libitum. In Experiments 1 and 2 Ivermectin in the form of a 1% w/v cattle injection ("Ivomec" ®, Merck, Sharp and Dome, B. V., Haarlem, Netherlands) was used; in Experiment 3, Ivermectin extracted from this commercial formulation was used, and this extract also served as the standard for the analytical procedure (the extraction efficiency was about 90%).

Experiment 1

"Ivomec" (1 ml., containing 10 mg. Ivermectin) was injected subcutaneously into two male lambs (#657 and #651) and one female lamb (#775). Venous blood samples (10 ml.) were taken from the jugular vein of each lamb before administration of the medicament and then at 1, 2 and 4 hours thereafter. Blood samples were then taken every morning for the next 5 days.

Experiment 2

This experiment was carried out on two male lambs (#663 and #671) and one female lamb (#763). To the left ear of each lamb, and without shaving or preparing the skin surfaces in any manner, there was attached an AV-DDS device containing as matrix a 4 mm. thick Spontex ® absorbent sponge in which circular perforations of 4 mm. diameter were made, the centers of which were approximately 8 mm. apart. The surface area of each matrix was 110 cm.$^2$, i.e. 55 cm.$^2$ applied to the outer and inner surfaces of the ear, respectively. Each matrix was impregnated prior to attachment, with 16 ml. soybean oil. Three layers of absorbent paper towels, perforated in the same manner as the sponge, were then attached to each matrix, the paper towels being impregnated with 16 ml. of "Ivomec". Thus each matrix contained approximately 160 mg. of Ivermectin, the preparation being referred to herein as "dosage form "A". The system was maintained on lamb #663 for 7 consecutive days, on lamb #671 for 16 consecutive days, and on lamb #763 for 18 consecutive days. Venous blood samples (10 ml.) were taken from the jugular vein of each lamb before administration of the medicament and then at 1, 2 and 4 hours thereafter. Blood samples were then taken every morning for the next 8, 17 and 18 days, respectively.

Experiment 3

This experiment was carried out on two female lambs (#760 and #778) and one male lamb (#665). A composition containing Ivermectin which had been extracted from "Ivomec" according to Oehler and Miller (Journal of the Association of Official Analytical Chemists, USA, 1989, 72(1): 59) was prepared (and determined on HPLC, the lower limit of detection being 3 ng./ml.). In order to prepare the composition, this extract containing about 90% Ivermectin was dissolved in soybean oil to give a concentration of medicament of approximately 10 mg./ml. To the left ear of each lamb, and without shaving or preparing the skin surfaces in any manner, there was attached an AV-DDS device containing as matrix a 4 mm. thick Spontex ® absorbent sponge in which circular perforations of 4 mm. diameter were made, the centers of which were approximately 8 mm. apart. The surface area of each matrix was 110 cm.$^2$, i.e. 55 cm.$^2$ applied to the outer and inner surfaces of the ear, respectively. Each matrix was impregnated prior to attachment, with 8 ml. soybean oil, allowed to stand for several minutes, and then impregnated with 16 ml. of the composition. Thus each matrix contained approximately 160 mg. of Ivermectin, the preparation being referred to herein as "dosage form "B". The system was maintained on each lamb for 17 consecutive days. Venous blood samples (10 ml.) were taken from the Jugular vein of each lamb before administration of the medicament and then at 1, 2 and 4 hours thereafter. Blood samples were then taken every morning for the next 19 days.

Results

Ivermectin serum concentrations, as determined by HPLC, are shown in Table 7, below. Prior to administration of the medicament, no Ivermectin could be detected in any of the lambs' sera.

In Experiment 1, each of the three lambs was injected subcutaneously with 10 mg. Ivermectin, which was first detected in blood samples taken 4 hours after administration in lamb #651, and in blood samples taken 24 hours after injection in lambs #657 and #775. Ivermectin was detected in blood samples taken up to day 4 in lamb #651 and up to day 5 in lambs #657 and #775.

In Experiment 2, the three lambs were treated with dosage form "A" as described; no Ivermectin could be detected in any of the blood samples.

In Experiment 3, using dosage form "B", Ivermectin was detected in blood samples taken from lamb #665, from 4 hours after administration up to day 13; in lamb #760, from 24 hours up to day 17; and in lamb #778, after day 2 and up to day 14.

Discussion of results

Owing to the fact that pure Ivermectin could not be readily obtained, it was necessary to extract this medicament as an approximately 90% pure product, from the commercially available formulation, as described above, in order to prepare dosage form "B" and to serve as the standard for the analytical procedure. Since Ivermectin has been reported as having the property of binding to many surfaces including glass and plastics, it seems likely that the Ivermectin serum concentrations reported in the present study were probably underestimates because the analysis vessels were not coated to prevent such binding. In spite of these difficulties, it may be concluded that, in accordance with the invention, Ivermectin can be administered transdermally to sheep for an extended period of time, as demonstrated in Experiment 3, above, in which dosage form "B" was incorporated into the AV-DDS device as described. Given the primitive nature of this dosage form, it was demonstrated that Ivermectin can be administered transdermally for 13 days, and perhaps even for a longer period.

The advantage of transdermal administration of Ivermectin in accordance with the invention is that serum concentrations of this medicament can be maintained for at least 13 days and that the treatment can be readily terminated, by simply removing the system from the animal's ear. Ease of termination is of importance when the animal's milk or meat is intended for human consumption.

the invention, was adsorbed in a matrix, which was incorporated into the AV-DDS device as previously described in detail herein.

In the first experiment, performed on two male lambs, 800 mg MPA was stirred overnight at 37° C. with 70 ml. soybean oil, the mixture impregnated into the 110 cm.$^2$ perforated sponge matrix (55 cm.$^2$ applied to the outer and inner ear surfaces), so that each such matrix contained 182.86 mg. MPA. Two such matrices were used per animal, one for each ear simultaneously, and were maintained on the ears for 11 consecutive days; the ear surfaces were not shaved or prepared in any manner prior to applying the devices incorporating the matrices. Venous blood samples (10 ml.) were taken from the jugular vein of each lamb before application of the devices, then 1, 2 and 4 hours thereafter and every morning (0700–0800) for the next 13 days.

In the second experiment, performed on two male and two female lambs, a larger amount of MPA was used, resulting in a concentration of 25 mg. MPA/ml. in soybean oil. Each perforated sponge was in this case impregnated with 8 ml. soybean oil, allowed to stand several minutes, then impregnated with 8 ml. of the MPA-containing composition. Three layers of absorbent paper towels perforated in the same manner as the sponge were attached to each system to cover the sponge, the perforated towels were impregnated with 16 ml. of the MPA-containing composition, whereby each dosage form contained 600 mg. MPA. The system, assembled as before, was mounted on the left ear, and maintained on the animals for 9 and 11 days, respec-

TABLE 7

| Mode of Administration | Ivermectin Serum Concentration (ng./ml.) | | | | | | | | |
|---|---|---|---|---|---|---|---|---|---|
| | subcutaneous injection | | | dosage form "A" | | | dosage form "B" | | |
| Lamb # | 651 | 657 | 775 | 663 | 671 | 763 | 665 | 760 | 778 |
| Time | | | | | | | | | |
| 0 | 0 | 0 | 0 | 0 | 0 | 0 | 0 | 0 | 0 |
| 1 hour | 0 | 0 | 0 | 0 | 0 | 0 | 0 | 0 | 0 |
| 2 hours | 0 | 0 | 0 | 0 | 0 | 0 | 0 | 0 | 0 |
| 4 hours | 9 | 0 | 0 | 0 | 0 | 0 | * | 0 | 0 |
| Day 1 | — | 20 | 6 | 0 | 0 | 0 | 8 | 15 | 0 |
| Day 2 | 14 | 17 | 42 | 0 | 0 | 0 | 14 | 17 | 4 |
| Day 3 | 19 | 8 | 15 | 0 | 0 | 0 | 14 | 18 | 5 |
| Day 4 | 6 | — | 14 | 0 | 0 | 0 | 12 | 18 | 6 |
| Day 5 | 0 | 15 | 49 | 0 | 0 | 0 | 9 | 14 | 4 |
| Day 6 | | | | 0 | 0 | 0 | 8 | 11 | 4 |
| Day 7 | | | | 0 | 0 | 0 | 8 | 13 | 7 |
| Day 8 | | | | 0 | 0 | 0 | 7 | 16 | 4 |
| Day 9 | | | | 0 | 0 | 0 | 6 | 7 | 4 |
| Day 10 | | | | 0 | 0 | 0 | 6 | 6 | * |
| Day 11 | | | | 0 | 0 | 0 | * | 6 | * |
| Day 12 | | | | 0 | 0 | 0 | * | * | * |
| Day 13 | | | | 0 | 0 | 0 | * | * | * |
| Day 14 | | | | 0 | 0 | 0 | 0 | * | * |
| Day 15 | | | | 0 | 0 | 0 | 0 | * | 0 |
| Day 16 | | | | 0 | 0 | 0 | 0 | * | 0 |
| Day 17 | | | | 0 | 0 | 0 | 0 | * | 0 |
| Day 18 | | | | | | 0 | — | 0 | 0 |
| Day 19 | | | | | | | 0 | 0 | 0 |

*trace

EXAMPLE VIII

Continuous Transdermal Administration of Medroxyprogesterone Acetate to Sheep Method The study was conducted on a farm located in the central plain region of Israel during October-November, 1990. Six lambs were fed once a day with commercially available concentrated feed pellets; hay and water were available ad libitum. Two experiments were performed. In each experiment a different medroxyprogesterone acetate (MPA) dosage form, in accordance with tively, in the case of the two male lambs, and for 15 days in the case of the female lambs. Venous blood samples (10 ml.) were taken from the jugular vein of each lamb before application of the devices, then 1, 2 and 4 hours thereafter and every morning (0700–0800) until the system was removed, and in certain cases after removal of the system. Bioavailability of MPA was determined by assaying the MPA serum concentrations, determined by a gas chromatographic method having a lower limit of detection of 0.25 ng./ml. (PPB).

Results

No MPA could be detected in the serum of any of the lambs, prior to attachment of the system. In the first experiment (see FIG. 20), MPA was detected in blood samples from one lamb (#99) one hour after the device was applied, and in the other lamb (#96) after 4 hours. MPA was detected in blood from lamb #96 throughout the 11-day treatment period and in blood from lamb #99 during 10 days. 48 hours after the device was removed from lamb #96, MPA could not be detected.

In the second experiment (see FIG. 21), the results were similar to the first experiment, with the following differences. In lamb #770, MPA was detected in the blood sample one hour after the device was mounted, while in the other 3 lambs MPA was similarly detected two hours after mounting the devices. In the female lambs (#770 and #771) the duration of treatment was 15 days and MPA was detected throughout the period for lamb #770, while for lamb #771 it was detected for 14 days. 24 hours after the device was removed, no MPA was detected in blood samples taken from any of the four lambs.

Discussion of results

Prior to the treatment with the device containing an MPA dosage form, no MPA could be detected in any of the blood samples taken from the lambs. In most of the blood samples taken 2 hours after treatment commenced, and in all of the blood samples taken 4 hours after treatment commenced, MPA was detected. MPA serum concentrations ranged from 0.25 ng./ml. (lower limit of detection) to 2.0 ng./ml. in blood samples taken during the treatment period. Both the first and second experiments gave similar results.

The results of this study demonstrate that, in accordance with the invention, MPA can be administered transdermally for an extended period of time to sheep and can provide a better alternative to the vaginal sponge method for synchronization in sheep. The present invention as applied to the administration of MPA to sheep provides the following advantages over the vaginal sponge method:

1. the present method involves no risk of infertility due to infection and/or physical damage to the internal sexual organs of the treated ewe;
2. the present method involves no risk of treatment failure which can occur in the existing method because of the risk of the sponge falling out, whereas with the present invention should the device become detached it can readily be observed and remounted;
3. the present method enables treatment to be discontinued at will by removal of the device, without the risk associated with the existing method of the string tearing and the consequent difficulty of removing the sponge;
4. the present method avoids changes in the milieu of the reproductive tract.

EXAMPLE IX

Transdermal Administration of Medroxyprogesterone Acetate to Ewes for the Induction of Synchronized Oestrus

Introduction

The method in common use today to achieve synchronized oestrus in sheep, is to insert an impregnated sponge into the vagina and maintain it therein for 10–13 days. The sponge is typically impregnated with flugestone acetate or medroxyprogesterone acetate, which are absorbed in the vagina and which subject the ewe to a progestational action comparable with the luteal phase of the sexual cycle; this action ceases when the sponge is removed. The present example provides an evaluation of the technique of the invention, when used to artificially induce oestrus to ewes at the end of the normal breeding season under field conditions.

Method

The study was performed over a period of 13 consecutive days in the last week of 1990 and the first week of 1991, on 24 sexually mature Merino/Cambridge ewes of proven fertility, at the end of the normal breeding season. The ewes, which were housed in a sheep shed in the central plain region of Israel, were maintained on an adequate nutritional diet, water being available ad libitum. Of the 24 ewes, 22 were treated with medroxyprogesterone acetate (MPA) according to the known intravaginal method, while the other 2 were treated with MPA according to the present invention. At the end of the 13-day period, each ewe was injected with 600 i.u. of PMSG (Intervet), oestrus being determined 48 hours later by the standing heat method; ewes exhibiting oestrus were then artificially inseminated.

The MPA dosage form was prepared and used in the following way. A mixture of MPA (Sigma) with soybean oil (23 mg./ml.) was heated to 37° C. and stirred overnight. To each of two ear devices, produced in a pilot production facility, a single matrix was attached, each matrix having a surface area of approximately 110 cm.$^2$ (i.e. 55 cm.$^2$ applied to the inner and to the outer ear surface) and consisting of 4 mm. thick Spontex ® absorbent sponge containing 4 mm. diameter circular perforations, the centers of which were approximately 8 mm. apart. Each matrix was impregnated first with 8 ml. soybean oil and then, after several minutes, with 8 ml. of the MPA/soybean oil admixture. Three layers of absorbent paper towels perforated in the same manner as the sponges were then laid over the latter and impregnated with 16 ml. of the MPA/soybean oil admixture, thus each dosage form contained $23 \times 24 = 552$ mg. MPA. As indicated, the device containing the MPA/soybean oil admixture was mounted on the animal's ear and kept in place 13 consecutive days; the skin surfaces of the ear had not previously been shaved or otherwise prepared.

Results

At the end of the 13-day period, the intravaginal sponges were removed (but had fallen out from 3 of the 22 ewes) and the ear devices were detached. Oestrus was observed in 21 of the total of 24 ewes, i.e. in all except the 3 from which the sponges had fallen out. The present study showed that the transdermal procedure in accordance with the invention was capable of achieving synchronized oestrus in ewes under field conditions. The present transdermal procedure has the advantages over the intravaginal method listed in the preceding example.

While particular embodiments of the invention have been particularly shown and/or described hereinabove, it will be appreciated that the present invention is not limited thereto, since, as will be readily apparent to skilled persons, many variations and modifications can be made. Accordingly, the essential concept, spirit and scope of the present invention will be better understood in the light of the claims which follow.

We claim:

1. In a non-adhesive matrix for use as a dosage form in the transdermal administration of a medicament to a mammal which comprises a porous, non-adhesive, absorbent perforate solid support having absorbed thereon a mixture comprising a medicament adapted for transdermal administration and a pharmaceutically acceptable carrier for the medicament, the improvement being that the carrier consists essentially of at least one compound selected from the group consisting of esters of $C_{8-24}$ fatty acids with at least one aliphatic hydroxy compound containing 2-12 carbon atoms and 2-3 hydroxy groups; and the acid component of the ester is selected from the group consisting of caprylic, capric, lauric, palmic, stearic, arachidic, behenic, lignoceric, oleic, elaidic, petroselinic, linoleic, alpha-linolenic, gamma-linolenic, linolelaidic, arachidic, 11-eicosenoic, 11,14-eicosadienoic, 11,14,17-eicosatrienoic, 8,11,14-eicosatrienoic, arachidonic, 5,8,11,14,17-eicosapentaenoic, erucic and nervonic acids;

provided that when said hydroxy compound is glycerol the esters thereof are selected from diglycerides and triglycerides of at least one $C_{8-24}$ fatty acid, whereby said medicament is detectable in the bloodstream within two hours after administration thereof.

2. A matrix according to claim 1, wherein the medicament comprises at least one member selected from the group consisting of growth promoters, fertility agents, micronutritional supplements, anti-inflammatory agents, anthelmintics, antibiotics and antiparasitics.

3. A matrix according to claim 1, which contains an additional medicament selected from antiinflammatory agents and antihistamines.

4. A matrix according to claim 1, wherein the medicament comprises at least one member selected from the group consisting of:
   (a) fertility and growth promoting agents: estradiol, flugestone acetate, medroxyprogesterone, medroxyprogesterone acetate, megestrol acetate, progesterone, proligestone, melengestrol acetate, testosterone, trenbulone, zeranol;
   (b) anthelmintics: albendazole, febantel, fenbendazole, flubendazole, ivermectin, levamisole, mebendazole, oxybendazole, oxfendazole, thiabendazole, tricalbendazole, pyrantel, morantel;
   (c) antibiotics: semisynthetic penicillins, tetracyclines and cephalosporins;
   (d) antiparasitics: cythioate, fenthion;
   (e) antiinflammatory agents: betamethazone, flumethazone, dexamethazone;
   (f) micronutrients: selenium disulfide, iron dextran.

* * * * *